United States Patent
Humphreys

(10) Patent No.: US 9,005,312 B2
(45) Date of Patent: Apr. 14, 2015

(54) BIO-OIL PRODUCTION METHOD

(75) Inventor: Len Humphreys, Roseville Chase (AU)

(73) Assignee: Licella Pty Ltd, Somersby (AU)

( * ) Notice: Subject to any disclaimer, the term of this patent is extended or adjusted under 35 U.S.C. 154(b) by 483 days.

(21) Appl. No.: 13/121,960

(22) PCT Filed: Oct. 1, 2009

(86) PCT No.: PCT/AU2009/001312
§ 371 (c)(1),
(2), (4) Date: Mar. 31, 2011

(87) PCT Pub. No.: WO2010/037178
PCT Pub. Date: Apr. 8, 2010

(65) Prior Publication Data
US 2011/0209387 A1    Sep. 1, 2011

Related U.S. Application Data

(60) Provisional application No. 61/101,805, filed on Oct. 1, 2008.

(51) Int. Cl.
| | | |
|---|---|---|
| *C10L 1/00* | (2006.01) | |
| *C12P 19/02* | (2006.01) | |
| *C10L 1/02* | (2006.01) | |
| *C12P 7/10* | (2006.01) | |
| *C12P 7/16* | (2006.01) | |
| *C12P 7/18* | (2006.01) | |

(52) U.S. Cl.
CPC . *C12P 19/02* (2013.01); *C10L 1/02* (2013.01); *C12P 7/10* (2013.01); *C12P 7/16* (2013.01); *C12P 7/18* (2013.01); *Y02E 50/16* (2013.01); *Y02E 50/10* (2013.01)

(58) Field of Classification Search
USPC ............ 44/307, 302, 308, 605; 210/634, 708, 210/774, 804, 806, 180, 350; 422/187, 261; 554/20, 21, 1, 175; 241/81; 494/36, 37
See application file for complete search history.

(56) References Cited

U.S. PATENT DOCUMENTS

| | | |
|---|---|---|
| 2004/0016525 A1 | 1/2004 | Gervais |
| 2006/0177917 A1 | 8/2006 | Warzywoda et al. |
| 2008/0057555 A1 | 3/2008 | Nguyen |
| 2009/0062516 A1 | 3/2009 | Belanger et al. |
| 2011/0173875 A1* | 7/2011 | Kleinert et al. ................. 44/300 |

FOREIGN PATENT DOCUMENTS

| | | |
|---|---|---|
| WO | WO 2007/120210 | 10/2007 |
| WO | WO 2008/017145 | 2/2008 |

(Continued)

OTHER PUBLICATIONS

Patent Abstract of Japan, JP 2005-296906 (Toyota Tsusho Corp et al) Oct. 27, 2005, p. 1.

(Continued)

*Primary Examiner* — Prem C Singh
*Assistant Examiner* — Chantel Graham
(74) *Attorney, Agent, or Firm* — Saliwanchik, Lloyd & Eisenschenk

(57) ABSTRACT

The invention relates to methods for the conversion of lignocellulosic matter into fuel products. More specifically, the invention relates to methods for the generation of a bio-oil product from specific component(s) of lignocellulosic matter.

21 Claims, 5 Drawing Sheets

(56) References Cited

FOREIGN PATENT DOCUMENTS

| WO | WO 2008/019228 | 2/2008 |
| WO | WO 2008/084490 | 7/2008 |
| WO | WO 2008/098032 | 8/2008 |

OTHER PUBLICATIONS

Patent Abstract of Japan, JP 2001-205070 (Japan Science & Technology Corp) Jul. 31, 2001, p. 1.

* cited by examiner

BIO-OIL PRODUCTION METHOD

CROSS-REFERENCE TO RELATED APPLICATIONS

This application is the U.S. national stage application of International Patent Application No. PCT/AU2009/001312, filed Oct. 1, 2009, which claims the benefit of U.S. Provisional Patent Application No. 61/101,805, filed Oct. 1, 2008.

TECHNICAL FIELD

The invention relates to methods for the conversion of lignocellulosic matter into fuel products. More specifically, the invention relates to methods for the generation of a bio-oil product from specific component(s) of lignocellulosic matter.

BACKGROUND

With the continuing high price of oil and its increasing importation costs in many countries, the production of alternative fuel products ("biofuels") is becoming increasingly important. A significant amount of research in the field has focussed on the conversion of lignocellulosic matter into fuel products such as ethanol to provide an alternative and renewable feedstock to the depleting sources of hydrocarbon-based raw materials.

Lignocellulosic matter consists of carbohydrate polymers (celluloses and hemicelluloses) and the phenolic polymer lignin. Existing technologies for the conversion of lignocellulosic matter into fuel products generally utilize a series of steps involving fractionation of the biomass followed by saccharification and fermentation. The saccharification and fermentation steps are often complex and add significantly to the cost of the process. Further, the hydrolysis of cellulose and hemicellulose into simple sugars suitable for fermentation is significantly hindered by the presence of tightly bound lignin. Existing technologies expend significant energy in decreasing the lignin content of sugar-containing fractions in order to increase accessibility by hydrolytic enzymes.

Lignin makes up a significant proportion of lignocellulosic matter and offers another utilizable resource in addition to the cellulosic and hemicellulosic components. However, a large proportion of biomass conversion methods fail to effectively utilize the lignin component which instead goes to waste. Additionally, many of the existing processes yield only ethanol. While ethanol is usable as a fuel, the energy content on a volume basis is about 30% less than currently used fossil fuels, and is not practical in current diesel engines. Ethanol also attracts water, which makes storage and handling difficult.

A need exists for improved methods of converting lignocellulosic matter into energy-containing products such as biofuels. A need also exists for biofuel production methods that better exploit the energy-producing potential of lignin.

SUMMARY OF THE INVENTION

In a first aspect, there is provided a method for solvating lignocellulosic biomass, the method comprising the steps of
(a) fractionating hemicellulose from the biomass with a solvent,
(b) removing fractionated hemicellulose from biomass remaining after step (a); and
(c) solvating lignin and cellulose from the remaining biomass with a solvent.

In a second aspect, there is provided a method for producing a bio-oil product from lignocellulosic biomass, the method comprising the steps of:
(a) fractionating hemicellulose from the biomass with a solvent,
(b) removing fractionated hemicellulose from biomass remaining after step (a); and
(c) solvating lignin and cellulose from the biomass remaining after step (a) with a solvent,
wherein the solvating in step (c) produces the bio-oil product.

In a third aspect, there is provided a method for producing a bio-oil product from lignocellulosic biomass, the method comprising the steps of:
(a) fractionating hemicellulose from the biomass with a solvent,
(b) removing fractionated hemicellulose from biomass remaining after step (a);
(c) fractionating either of:
  (i) lignin
  (ii) cellulose
  from the biomass remaining after step (a); and
(d) solvating either or both of the lignin and cellulose of step (c),
wherein the solvating in step (d) produces the bio-oil product.

In one embodiment of the third aspect, the fractionating in step (c) is performed using an alcohol, an aqueous alcohol, or water. The alcohol, aqueous alcohol, or water may be used to fractionate the lignin or cellulose under supercritical conditions.

In one embodiment of the first, second or third aspect, fractionating of hemicellulose in step (a) is performed using sub-critical water.

In another embodiment of the first, second or third aspect, fractionating of hemicellulose using sub-critical water is performed at a temperature of between about 100° C. and about 300° C.

In an additional embodiment of the first, second or third aspect, fractionating of hemicellulose using sub-critical water is performed at a pressure of between about 2 MPa (20 bar) and about 4 MPa (40 bar).

In a further embodiment of the first, second or third aspect, fractionating of hemicellulose using sub-critical water is performed at about 190° C. and about 3 MPa (30 bar).

In one embodiment of the first, second or third aspect, the fractionated hemicellulose component of step (b) is subjected to saccharification to produce a fermentable saccharide. The saccharide may be fermented to produce an alcohol selected from the group consisting of ethanol, butanol, xylitol, mannitol, and arabinol.

In a fourth aspect, there is provided a method for producing a bio-oil product, the method comprising the step of solvating a material comprising either or both of:
(i) lignin;
(ii) cellulose,
using a solvent, wherein said solvating produces the bio-oil product.

In one embodiment of the first, second, third or fourth aspect, the solvating is performed using a solvent that is an alkylating agent. The alkylating agent may be selected from the group consisting of an alkylhalide, an alkylsulfate, an olefin, and an alkylphosphate. The alkylating agent may be an alcohol. The alcohol may be a C1 to C6 alcohol. The C1 to C6 alcohol may be ethanol, methanol, or butanol.

The solvent may be aqueous. The aqueous solvent may comprise at least one percent water based on total weight of solvent. The aqueous solvent may comprise at least 80 percent water based on total weight of solvent. The aqueous solvent may comprise at least 90 percent water based on total weight of solvent.

In one embodiment of the first, second, third or fourth aspect, the solvating is performed at a temperature of between about 230° C. and about 360° C.

In another embodiment of the first, second, third or fourth aspect, the solvating is performed at a pressure of between about 14 MPa (140 bar) and about 24 MPa (240 bar).

In one embodiment of the first, second, third or fourth aspect, the solvating is performed at a temperature of between about 230° C. and about 360° C., and at a pressure of between about 14 MPa (140 bar) and about 24 MPa (240 bar).

In another embodiment of the first, second, third or fourth aspect, the solvating is performed at a temperature of about 320° C. and a pressure of about 18 MPa (180 bar).

In one embodiment of the second, third or fourth aspect, the step of solvating converts substantially all of the lignin into the bio-oil product.

In one embodiment of the second, third or fourth aspect, the step of solvating converts substantially all of the cellulose into the bio-oil product.

In one embodiment of the second, third or fourth aspect, the step of solvating converts substantially all of the cellulose and substantially all of the lignin into the bio-oil product.

In a fifth aspect, there is provided a bio-oil product obtainable by the method of the first, second, third or fourth aspect.

In a sixth aspect, there is provided a bio-oil product obtained by the method of the first, second, third or fourth aspect.

The bio-oil product of any of the previous aspects may be used as a biofuel, or a biofuel additive.

In a seventh aspect, there is provided a method for producing a bio-oil from lignocellulosic matter, the method comprising the steps of:
  (a) solvating hemicellulose from the lignocellulosic matter using a solvent,
  (b) removing solvated hemicellulose from solid matter remaining after step (a); and
  (c) solvating lignin and cellulose from the solid matter remaining after step (a) using a solvent,
wherein step (c) of solvating lignin and cellulose produces the bio-oil.

In one embodiment of the seventh aspect, the lignocellulosic matter comprises 10%-35% hemicellulose, 15%-45% cellulose and 2%-35% lignin.

In one embodiment of the seventh aspect, the lignocellulosic matter comprises 20%-35% hemicellulose, 20%-45% cellulose and 20%-35% lignin.

In another embodiment of the seventh aspect, the solvent of step (c) is an aqueous alcohol comprising no more than ten carbon atoms.

In one embodiment of the seventh aspect, the aqueous alcohol is ethanol or methanol.

In an additional embodiment of the seventh aspect, the aqueous alcohol comprises 1%-30% alcohol by weight.

In another embodiment of the seventh aspect, the aqueous alcohol comprises 5%-30% alcohol by weight.

In one embodiment of the seventh aspect, the aqueous alcohol comprises about 25% alcohol by weight.

In another embodiment of the seventh aspect, the aqueous alcohol comprises about 20% alcohol by weight.

In one embodiment of the seventh aspect, step (c) is performed at a reaction temperature of between 250° C. and 400° C.

In another embodiment of the seventh aspect, step (c) is performed at a reaction temperature of between 280° C. and 350° C.

In one embodiment of the seventh aspect, step (c) is performed at a temperature of about 320° C.

In one embodiment of the seventh aspect, step (c) is performed at a reaction pressure of between 12 MPa and 24 MPa.

In another embodiment of the seventh aspect, step (c) is performed at a reaction pressure of about 20 MPa.

In one embodiment of the seventh aspect, the lignin and cellulose of step (c) is in the form of a slurry.

In one embodiment of the seventh aspect, the slurry comprises between 2% and 45% solid matter by weight.

In one embodiment of the seventh aspect, the slurry comprises between 2% and 30% solid matter by weight.

In a further embodiment of the seventh aspect, the slurry comprises about 5% solid matter by weight.

In one embodiment of the seventh aspect, step (c) is performed for between 2 minutes and 60 minutes.

In one embodiment of the seventh aspect, step (c) is performed for between 2 minutes and 40 minutes.

In another embodiment of the seventh aspect, step (c) is performed for between 5 minutes and 30 minutes.

In one embodiment of the seventh aspect, the solvating of hemicellulose in step (a) is performed at a reaction temperature of between 100° C. and 250° C., and a reaction pressure of between 0.2 MPa and 5 MPa.

In a further embodiment of the seventh aspect, the solvent of step (a) is an aqueous acid and the treatment is performed at a pH of below about 6.5.

In one embodiment of the seventh aspect, the solvent of step (a) is an aqueous base and the treatment is performed at a pH of above about 7.5.

In one embodiment of the seventh aspect, the solvent of step (a) is water.

In one embodiment of the seventh aspect, the method further comprises pre-treating the lignocellulosic matter prior to solvating hemicellulose in step (a).

In an additional embodiment of the seventh aspect, the pre-treating comprises producing a shiny comprising a mixture of a solvent and particles derived from the lignocellulosic matter.

In one embodiment of the seventh aspect, the particles are between about 50 microns and about 500 microns in size.

In one embodiment of the seventh aspect, the particles are between about 100 microns and about 400 microns in size.

In one embodiment of the seventh aspect, the slurry comprises between about 5% and about 20% lignocellulosic matter.

In a further embodiment of the seventh aspect, the lignin is fractionated from the solid matter remaining after step (a) prior to performing step (c) of solvating to produce the bio-oil.

In one embodiment of the seventh aspect, the cellulose is fractionated from the solid matter remaining after step (a) prior to performing step (c) of solvating to produce the bio-oil.

In one embodiment of the seventh aspect, the solvated hemicellulose removed in step (b) is subjected to saccharification to produce a fermentable saccharide.

In an additional embodiment of the seventh aspect, the saccharide is fermented to produce an alcohol selected from the group consisting of ethanol, butanol, xylitol, mannitol, and arabinol.

In an eighth aspect, there is provided a method for producing a bio-oil product from a material comprising lignin and cellulose, the method comprising treating the material with a supercritical aqueous alcohol at a reaction temperature of between 180° C. and 350° C. and a reaction pressure of between 8 MPa and 26 MPa, wherein said treating solvates the lignin and cellulose producing the bio-oil product.

In one embodiment of the eighth aspect, the material is treated at a reaction temperature of between 280° C. and 350° C. and a reaction pressure of between 12 MPa and 24 MPa.

In one embodiment of the eighth aspect, the aqueous alcohol comprises 1% to 30% alcohol by weight.

In one embodiment of the eighth aspect, the aqueous alcohol comprises 5% to 30% alcohol by weight.

In another embodiment of the eighth aspect, the aqueous alcohol is ethanol.

In a ninth aspect, there is provided a bio-oil obtainable by the method of the seventh or eighth aspect.

In a tenth aspect, there is provided a bio-oil obtained by the method of the seventh or eighth aspect.

BRIEF DESCRIPTION OF THE DRAWINGS

A preferred embodiment of the present invention will now be described, by way of an example only, with reference to the accompanying drawings wherein.

DEFINITIONS

Figure 1:
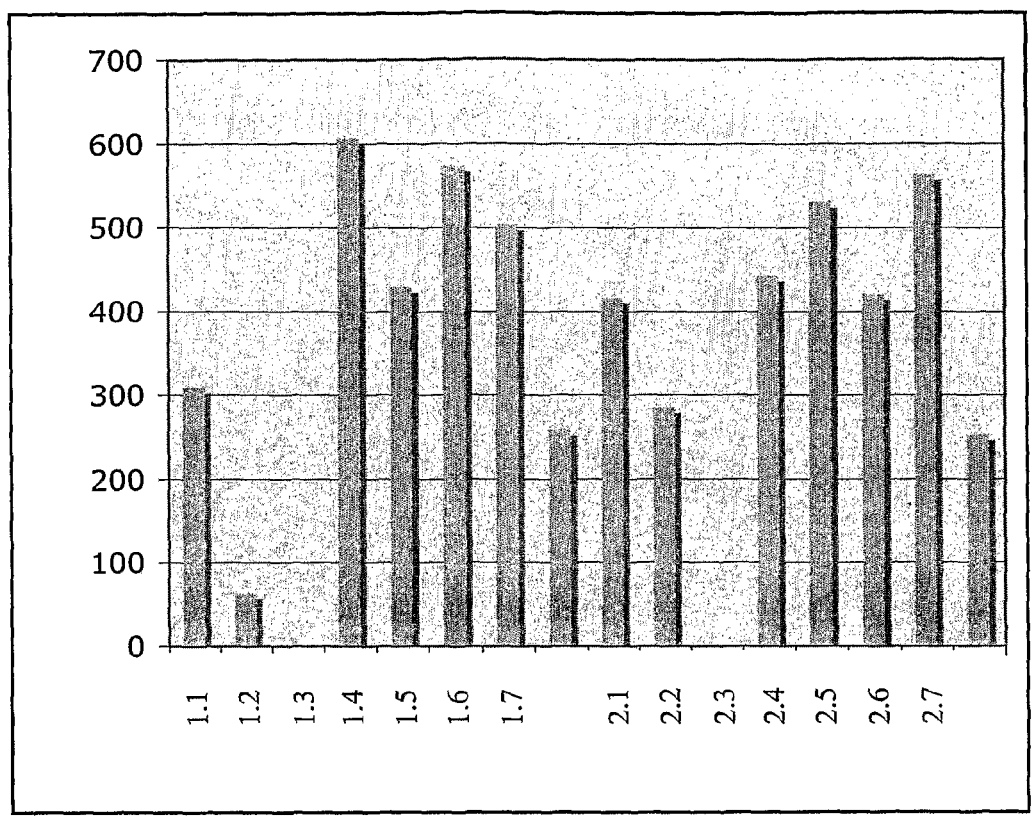
FIG. 1 is a graph showing the results of a dinitrosalicyclic acid (DNS) assay conducted on hemicellulose liquor samples subjected to saccharification using hydrolytic enzymes. Absorbance readings ($I_{540}$, in mOD) from substrate only controls and enzyme only controls were subtracted from readings obtained from enzyme-substrate samples. Sample numbers are shown on the horizontal axis. The vertical axis shows relative amounts of reducing sugars present in each sample.

As used in this application, the singular form "a", "an" and "the" include plural references unless the context clearly dictates otherwise. For example, the term "a particle" also includes a plurality of particles.

As used herein, the term "comprising" means "including." Variations of the word "comprising", such as "comprise" and "comprises", have correspondingly varied meanings. Thus, for example, a material "comprising" lignin and cellulose may consist exclusively of lignin and cellulose or may include other additional substances.

As used herein, the terms "lignocellulosic matter" and "lignocellulosic biomass" are used interchangeably and have the same meaning. The terms encompass any substance comprising lignin, cellulose, and hemicellulose.

As used herein, the term "aqueous solvent" refers to a solvent containing at least one percent water based on total weight of solvent.

As used herein, the term "aqueous ethanol" refers to an ethanol solvent containing at least one percent water based on total weight of solvent.

As used herein, the term "saccharide" encompasses any molecule comprising one or more monosaccharide units. Examples of saccharides include, but are not limited to, cellulose, hemicellulose, polysaccharides, oligosaccharides, disaccharides and monosaccharides. "Saccharides" also include glycoconjugates, such as glycoproteins and glycolipids. All stereoisomeric and enantiomeric forms of saccharides are encompassed by the term.

As used herein, a "supercritical" substance (e.g. a supercritical solvent) refers to a substance that is heated above its critical temperature and pressurised above its critical pressure (i.e. a substance at a temperature and pressure above its critical point). The term "supercritical" also encompasses conditions of temperature and/or pressure that are a small, although not substantial, amount (e.g. approximately 5%) below the critical point of the substance in question (i.e. "sub-critical"). Accordingly, the term "supercritical" also encompasses oscillatory behaviour around the critical point of a substance (i.e. movement from supercritical conditions to sub-critical conditions and vice versa). For example, a solvent having a critical point of 305 degrees Kelvin and 4.87 atmospheres may, for the purposes of the present invention, still be considered to be "supercritical" at a slightly lower temperature (e.g. between 290 degrees and 305 degrees Kelvin) and/or a slightly lower pressure (e.g. between 4.63 and 4.87 atmospheres).

It will be understood that use of the term "about" herein in reference to a recited numerical value (e.g. a reaction temperature, pressure or pH) includes the recited numerical value and numerical values within plus or minus ten percent of the recited value.

It will be understood that use of the term "between" when referring to a range of numerical values encompasses the numerical values at each endpoint of the range. For example, a temperature range of between 10° C. and 15° C. is inclusive of the temperatures 10° C. and 15° C.

Any description of prior art documents herein, or statements herein derived from or based on those documents, is not an admission that the documents or derived statements are part of the common general knowledge of the relevant art in Australia or elsewhere.

For the purposes of description all documents referred to herein are incorporated by reference unless otherwise stated.

DETAILED DESCRIPTION OF THE INVENTION

The invention provides methods for generating a bio-oil product from lignocellulosic matter without the need for enzymatic hydrolysis or fermentation. Lignocellulosic matter treated in accordance with the methods of the invention is generally subjected to a step of hemicellulose removal followed by direct conversion of the remaining matter (comprising predominantly lignin and cellulose) into a stable bio-oil product. The bio-oil product may be used directly, processed to generate other products (e.g. fuels), or used as a fuel additive. Hemicellulose separated in accordance with the methods of the invention may be converted into products such as alcohols.

Existing technologies have demonstrated that lignocellulosic matter may be solubilized with supercritical solvents. However, the products generated often contain significant amounts of tar-like compounds and are difficult to process. The three main components of lignocellulosic matter (i.e. lignin, cellulose and hemicellulose) are believed to have different reactivities. In particular, hemicellulose is thought to be prone to excessive conversions leading to highly unstable and/or charred materials, whereas the other two fractions (lignin and cellulose) are believed to react more slowly. The high temperatures associated with supercritical treatment are likely to induce the dissolution of hemicellulose well before lignin and cellulose react to a significant extent. The hemicellulose-derived sugars therefore dehydrate quickly, creating double bonds and highly reactive cyclic molecules (e.g. furfural) that easily polymerise and yield tar-like compounds if not stabilised. This significantly compromises the efficiency of subsequent steps (e.g. saccharification and fermentation) utilized in current technologies to generate biofuels. The methods of the invention circumvent this problem by providing an initial step of hemicellulose separation under mild conditions thereby minimizing sugar dehydration and the formation of tar-like molecules during the processing of the lignin and cellulose components.

The solubilisation of lignocellulosic matter using current technologies is generally a precursor to further saccharification and fermentation steps required for the production of biofuel. Those additional steps are often complex and add significantly to the cost of the process. In addition, saccharification of solubilized cellulose and/or hemicellulose into sugar chains of a suitable length for fermentation is generally hindered by the presence of tightly bound lignin. The methods of the invention circumvent this problem by facilitating the direct conversion of lignin and cellulose into a bio-oil product without the need for saccharification and fermentation steps.

Without being limited to a particular mechanism or mode of action, it is believed that treatment of matter comprising lignin and cellulose in accordance with the methods of the invention facilitates swelling of the lignin and/or cellulose and chemical stabilization of the bio-oil product formed, thus minimizing polymerization into tar-like compounds. Mechanical swelling of the cellulose and/or lignin is believed to assist in "opening up" the substrate making it more accessible for hydrolysis and depolymerization. Chemical stabilization of the bio-oil product may occur through various interactions including alkylation and scavenging of free-radicals. For example, the alkylation of reactive groups in cellulose and/or lignin is likely to prevent highly reactive species from polymerizing. In addition, scavenging of free-radicals by the solvent (e.g. via formation of hydroxy radicals and/or ethoxy radicals) may convert aromatic radicals into non-radical aromatics. This in turn may reduce the potential for cross-linking involving aromatics in the bio-oil product.

Accordingly, processing of lignocellulosic matter in accordance with the methods of the invention circumvents a number of deficiencies associated with existing bio-fuel production methods and also provides a means of exploiting the energy-producing potential of lignin.

Lignocellulosic Matter

The methods described herein are suitable for producing a bio-oil product from a material comprising lignin and cellulose. Any material comprising lignin and cellulose may be used. The material may comprise any number of substances in addition to lignin and cellulose. Alternatively, the material may consist predominantly of lignin and cellulose, or consist of lignin and cellulose only. In certain embodiments, material utilised in the methods of the invention additionally comprises proteins.

In certain embodiments, the material utilised in the methods of the invention is lignocellulosic matter. In general, lignocellulosic matter refers to a substance comprising the components of lignin, cellulose and hemicellulose.

The relative proportion of lignin, hemicellulose and cellulose in a given sample will depend on the nature of the lignocellulosic matter.

For example, in some embodiments lignocellulosic matter used in the methods of the invention comprises 2-35% lignin, 15-45% cellulose and 10-35% hemicellulose.

In other embodiments, lignocellulosic matter used in the methods of the invention comprises 20-35% lignin, 20-45% cellulose and 20-35% hemicellulose.

In other embodiments, the content of lignin in the lignocellulosic matter is more than 35%, or less than 20%, the content of cellulose is more than 45% or less than 20%, and the content of hemicellulose is more than 35% or less than 20%.

In some embodiments, the lignocellulosic matter comprises at least about 10% lignin, at least about 15% cellulose, and at least about 10% hemicellulose.

In other embodiments, the lignocellulosic matter comprises at least about 15% lignin, at least about 20% cellulose, and at least about 15% hemicellulose.

In additional embodiments, the lignocellulosic matter comprises at least about 20% lignin, at least about 25% cellulose, and at least about 20% hemicellulose.

In some embodiments, the lignocellulosic matter comprises at least about 25% lignin, at least about 30% cellulose, and at least about 25% hemicellulose.

The skilled addressee will recognize that the methods described herein are not constrained by the relative proportions of lignin, hemicellulose and cellulose in a given source of lignocellulosic matter.

Lignocellulosic matter for use in the methods of the invention may be derived from any source.

For example, woody plant matter may be used as a source of lignocellulosic matter. Examples of suitable woody plants include, but are not limited to, pine (e.g. *Pinus radiata*), birch, eucalyptus, bamboo, beech, spruce, fir, cedar, poplar, willow and aspen. The woody plants may be coppiced woody plants (e.g. coppiced willow, coppiced aspen).

By way of example only, the proportion of hemicellulose in woody plant matter may be between about 15% and about 40%, the proportion of cellulose may be between about 30% and about 60%, and the proportion of lignin may be between about 5% and about 40%. Preferably, the proportion of hemicellulose of the woody plant matter is between about 23% and about 32%, the proportion of cellulose between about 38% and about 50%, and the proportion of lignin between about 15% and about 25%. Additionally or alternatively, fibrous plant matter may be used as a source of lignocellulosic matter, non-limiting examples of which include grass (e.g. switchgrass), grass dippings, flax, corn cobs, corn stover, reed, bamboo, bagasse, hemp, sisal, jute, cannibas, hemp, straw, wheat straw, abaca, cotton plant, kenaf, rice hulls, and coconut hair.

Suitable agricultural sources of lignocellulosic matter include, but are not limited to, agricultural crops, crop residues, and grain processing facility wastes (e.g. wheat/oat hulls, corn fines etc.). In general, agricultural source materials may include branches, bushes, canes, corn and cornhusks, energy crops, forests, fruits, flowers, grains, grasses, herbaceous crops, leaves, bark, needles, logs, roots, saplings, short rotation woody crops, shrubs, switch grasses, trees, vines, hard woods and soft woods.

Additionally or alternatively, lignocellulosic matter may be derived from commercial or virgin forests (e.g. trees, saplings, scrap wood such as branches, leaves, bark, logs, roots and products derived from the processing of such materials).

Additionally or alternatively, products and by-products comprising lignocellulosic matter may be used as a source of lignocellulosic matter. Non-limiting examples include wood-related materials and woody wastes (e.g. agricultural residue, forestry or timber processing residue, waste or byproduct streams from wood products, sawmill and paper mill discards and off-cuts, sawdust, particle board and leaves) and industrial products (e.g. pulp, paper, papermaking sludge, cardboard, textiles and cloths, dextran, and rayon).

Lignocellulosic matter may optionally be pre-treated prior to performing the methods of the invention. For example, mechanical and/or chemical methods may be used to disrupt the structure of lignocellulosic matter. Non-limiting examples of mechanical pre-treatment methods include pressure, grinding, agitation, shredding, milling, compression/expansion, or other types of mechanical action. Pre-treatment of the lignocellulosic matter may be performed using a mechanical apparatus, for example, an extruder, a pressurized vessel, or a batch reactor.

Pre-treatment methods may include treatment with heat. For example, steam explosion pre-treatment methods may be used to disrupt the structure of lignocellulosic matter. In general, steam explosion pre-treatment methods involve exposing the matter to high pressure steam in a contained environment before the resulting product is explosively discharged to an atmospheric pressure. Pre-treatment with steam explosion may additionally involve agitation of the lignocellulosic matter.

In preferred embodiments, lignocellulosic matter for use in the methods of the invention is provided in the form of a slurry. The slurry may be generated, for example, by converting the lignocellulosic matter into a powder of appropriate particle size (e.g., by using grinding, agitation, shredding, milling, compression/expansion and/or other types of mechanical action) and mixing with an appropriate liquid (e.g. water or aqueous alcohol).

The particle size of solid matter included in the slurry may be between about 10 microns and about 10,000 microns. For example, the particle size of solid matter included in the slurry may be at least about 1000, 2000, 3000, 4000, 5000, 6000, 7000, 8000 or 9000 microns. Alternatively, the particle size may be between about 10 microns and 50 microns, between about 10 microns and about 100 microns, between about 10 microns and about 400 microns, between about 10 microns and about 500 microns, between about 100 microns and about 200 microns, between about 100 microns and about 300 microns, between about 100 microns and about 500 microns, or between about 100 microns and about 1000 microns.

In one embodiment, the particle size is between about 100 microns and about 400 microns.

In another embodiment, the particle size is between about 50 microns and about 500 microns.

In another embodiment, the solid matter is wood flour and the particle size is between about 150 microns and about 300 microns.

The concentration of solid matter in the slurry may be high (e.g. above about 50% w/v). Alternatively, the concentration of solid matter in the slurry may be between about 1% and about 50%, between about 1% and about 40%, between about 1% and about 30%, between about 1% and about 20%, or between about 1% and about 10% w/v.

In certain embodiments, the concentration of solid matter in the slurry is between about 5% and about 20% w/v.

In one embodiment, the solid matter is wood flour and the concentration of solid matter in the slurry is about 10% w/v.

In alternative embodiments, methods of the invention are conducted using a material comprising lignin without cellulose. As used herein a material comprising lignin "without" cellulose will be understood to include a material with no cellulose but also a material comprising a small amount of cellulose (as may be the case after purification or fractionation of lignin from a more complex material).

In another alternative embodiment, methods of the invention are conducted using a material comprising cellulose without lignin. As used herein a material comprising cellulose "without" lignin will be understood to include a material with no lignin but also a material comprising a small amount of lignin (as may be the case after purification or fractionation of cellulose from a more complex material).

One or more pre-treatment steps may be conducted to separate, up-concentrate and/or purify lignin and/or cellulose from a starting material comprising additional substances.

Fractionation of Hemicellulose

The methods of the invention may be used to generate a bio-oil product from any material comprising lignin and cellulose.

In certain embodiments, the material is lignocellulosic matter. In embodiments where the material is lignocellulosic matter, hemicellulose may be fractionated prior to converting lignin and cellulose into a bio-oil.

"Fractionation" of hemicellulose from lignocellulosic matter as contemplated herein refers to a process whereby hemicellulose is partially or wholly separated from other components (e.g. lignin and/or cellulose) of the same matter.

Following hemicellulose fractionation, the remaining solid matter comprising predominantly lignin and cellulose may be treated with a solvent to produce a bio-oil product using the methods of the invention.

In alternative embodiments, the remaining solid matter may be separated or substantially separated into lignin and cellulose components, either or both of which may be treated to produce an bio-oil product using the methods of the invention.

Lignocellulosic matter may optionally be pre-treated prior to hemicellulose fractionation, for example, as described in the section above entitled "Fractionation of lignocellulosic matter". The fractionation of hemicellulose from lignocellulosic matter will generally involve the cleavage of specific chemical bonds. For example, covalent cross-linkages between hemicellulose and lignin may be broken to facilitate the fractionation. This may involve the cleavage of ester linkages, for example, between the α-carbon of the phenylpropane subunit in lignin and the free carboxyl group of uronic acids and aromatic acids in hemicellulose.

Additionally or alternatively, cleavage of ester linkages between the α-carbon of the phenylpropane subunit in lignin and hydroxyls in hemicellulose such as L-arabinose (O-5), D-glucose or D-mannose (O-6), O-2 xylose, O-3 xylose or glycosidic hydroxyl (O-1) may also occur during fractionation of hemicellulose chains from lignin.

Fractionation of hemicellulose may also involve the cleavage of bonds existing between hemicellulose and cellulose (e.g. hydrogen bonds) and/or bonds within the structure of hemicellulose (e.g. β(1→4) linkages between monosaccharide units or α(1→6) side branch linkages).

Fractionation of hemicellulose in accordance with the methods of the invention will generally involve the use of one or more solvents. Any solvent capable of solvating hemicellulose can potentially be used, non-limiting examples of which include water, aqueous acidic solutions, aqueous alkaline solutions, and organic solvents. Suitable reaction conditions for the solvation of hemicellulose from lignocellulosic matter will depend on the specific solvent or solvents used, and the nature of the lignocellulosic starting material.

Preferably, hemicellulose fractionation is conducted under mild conditions thereby minimizing sugar dehydration and the formation of tar-like molecules through polymerization.

In preferred embodiments, the hemicellulose is fractionated by solvation in aqueous solution. In general, solvation of hemicellulose in aqueous solution will typically also involve partial hydrolysis of the hemicellulose. Examples of suitable aqueous solutions for the solvation and partial hydrolysis of hemicellulose include aqueous acidic solutions, aqueous alkaline solutions, and aqueous solutions of neutral pH (i.e. pH of about 7.0).

A suitable alkaline aqueous solution may have a pH of above about 7.0, or above about 7.5. For example, a suitable alkaline aqueous solution may have a pH of between about 7.0 and about 11.0. In certain embodiments, the alkaline aqueous solution has a pH of between about 7.0 and about 10.5, between about 8.0 and about 10.5, between about 7.0 and about 10.0, between about 7.0 and about 9.5, between about 7.0 and about 9.0, between about 7.0 and about 8.5, between about 7.0 and about 8.0, between about 7.2 and about 8.0, or between about 7.0 and 7.5.

A suitable acidic aqueous solution may have a pH of below about 7.0, or below about 6.5. For example, a suitable acidic aqueous solution may have a pH of between about 2.0 and about 7.0, or between about 3.0 and about 7.0. In certain embodiments, the acidic aqueous solution has a pH of between about 3.5 and about 6.0, between about 3.5 and about 7.0, between about 4.0 and about 7.0, between about 4.5 and about 7.0, between about 5.0 and about 7.0, between about 5.5 and about 7.0, between about 6.0 and about 7.0, between about 6.0 and about 6.8, or between about 6.5 and about 7.0.

In one preferred embodiment, hemicellulose is fractionated from lignocellulosic biomass in aqueous solution at neutral pH (i.e. pH 7.0) or substantially neutral pH.

In another preferred embodiment, hemicellulose is fractionated from lignocellulosic biomass in aqueous solution at a pH of between about 6.5 and about 7.5.

In another preferred embodiment, hemicellulose is fractionated from lignocellulosic biomass in acidic aqueous solution at a pH of about 2.0.

In most cases, the pH of the reaction mixture can be adjusted by adding a suitable acid or base.

Non-limiting examples of suitable acids that may be used to adjust the pH of a reaction mixture include hydrochloric acid, trifluoroacetic acid, sulfuric acid, sulfurous acid and organic acids such as propionic acid, lactic acid, citric acid, or glycolic acid. Additionally or alternatively, carbon dioxide may be added to the reaction mixture to obtain an acidic pH (i.e. a pH of below about 7.0).

Non-limiting examples of suitable bases that may be used to adjust the pH of a reaction mixture include sodium hydroxide, potassium hydroxide, ammonium hydroxide, carbonates and bicarbonates.

Methods by which the pH of a reaction mix may be determined are known in the art, and described, for example in Gallagher and Wiley (Eds) *Current Protocols Essential Laboratory Techniques* John Wiley & Sons, Inc (2008).

The solvation of hemicellulose in aqueous solution may be performed at any reaction temperature (in combination with any of the pH ranges or values referred to above). For example, the solvation of hemicellulose in aqueous solution may be performed at a reaction temperature of between about 120° C. and about 250° C. In certain embodiments of the invention, the reaction temperature is between about 130° C. and about 250° C., between about 140° C. and about 250° C., between about 150° C. and about 250° C., between about 160° C. and about 250° C., between about 170° C. and about 250° C., between about 180° C. and about 250° C., between about 190° C. and about 250° C., between about 200° C. and about 250° C., between about 210° C. and about 250° C., between about 220° C. and about 250° C., between about 230° C. and about 250° C., between about 240° C. and about 250° C., between about 120° C. and about 240° C., between about 120° C. and about 230° C., between about 120° C. and about 220° C., between about 120° C. and about 210° C., between about 120° C. and about 200° C., between about 120° C. and about 190° C., between about 120° C. and about 180° C., between about 120° C. and about 170° C., between about 120° C. and about 160° C., between about 120° C. and about 150° C., between about 120° C. and about 140° C. or between about 120° C. and about 130° C.

In one preferred embodiment, hemicellulose is fractionated from the lignocellulosic matter at reaction temperatures ranging from about 120° C. to about 190° C.

Suitable reaction temperatures may be obtained, for example, by performing the solvation of hemicellulose in a mechanical apparatus such as a batch reactor or pressurized vessel. Performing the solvation of hemicellulose in a mechanical apparatus, may also allow alteration of the pressure applied at the operating temperatures contemplated.

The solvation of hemicellulose in aqueous solution may be performed at any reaction pressure (in combination with any of the ranges/values of reaction temperatures and/or reaction pH referred to above).

For example, the solvation of hemicellulose in aqueous solution may be performed at a reaction pressure of between about 0.1 MPa (1 bar) and about 25 MPa (250 bar), between about 0.1 MPa (1 bar) and about 10 MPa (100 bar), between about 0.1 MPa (1 bar) and about 5 MPa (50 bar), preferably between about 0.2 MPa (2 bar) and about 5 MPa (50 bar), and more preferably between about 1 MPa (10 bar) and about 4 MPa (40 bar).

In a preferred embodiment, hemicellulose is fractionated from lignocellulosic matter at a reaction pressure of between about 0.2 MPa (2 bar) and about 5 MPa (50 bar).

In another preferred embodiment, hemicellulose is fractionated from lignocellulosic matter at a reaction pressure of between about 1 MPa (10 bar) and about 4 MPa (40 bar).

In general, reactions are performed for a period of time sufficient to solvate substantially all of the hemicellulose, or, the majority of hemicellulose from the lignocellulosic matter.

For example, a reaction may be performed under conditions defined by a combination of any of the ranges/values of reaction temperature, reaction pressure and/or reaction pH referred to above for less than 20 minutes. In some embodiments, the reaction is performed for between about 2 minutes and about 20 minutes. In other embodiments, the reaction is performed from between about 5 minutes and about 15 minutes. In other embodiments, the reaction is performed for a period of more than 20 minutes.

Optimal reaction conditions for the solvation of hemicellulose from lignocellulosic matter will ultimately depend on factors including the type of lignocellulosic matter under treatment and the specific solvent used. For example, factors such as temperature and pH of the reaction mixture, isotonicity, amount of lignocellulosic matter and solvent, and length of reaction time may be varied in order to optimise the reaction.

Optimal reaction conditions will be readily apparent to the skilled addressee upon analysis of the solvated hemicellulose, which may be performed using standard methods generally known in the art. For example, solvated hemicellulose may be analysed using spectroscopy techniques. Suitable spectroscopy techniques include, but are not limited to, near infra red spectroscopy, fourier transform infrared spectroscopy, nuclear magnetic resonance spectroscopy, raman microscopy, LTV microspectrophotometry and X-ray diffraction. Additionally or alternatively, solvated hemicellulose may quantified by high performance liquid chromatography, for example, using methods described in Bjerre et al., "*Quantification of solubilized hemicellulose from pretreated lignocellulose by acid hydrolysis and high performance liquid chromatography*", (1996) in publication Riso-R-855 (EN), Rise National Laboratory.

In one preferred embodiment, hemicellulose is fractionated from lignocellulosic matter at a reaction temperature of between about 100° C. and 250° C., and a reaction pressure of between about 0.2 MPa (2 bar) and about 5 MPa (50 bar). The pH of the reaction mix may be about 7.0, above about 7.0, or below about 7.0. The pH of the reaction mix may be about 2.0.

In another preferred embodiment, hemicellulose is fractionated from lignocellulosic matter at a reaction temperature of between about 100° C. and 250° C., and a reaction pressure of between about 1 MPa (10 bar) and about 4 MPa (40 bar). The pH of the reaction mix may be about 7.0, above about 7.0, or below about 7.0. The pH of the reaction mix may be about 2.0.

In another preferred embodiment, the hemicellulose component is fractionated from the lignocellulosic matter using water at a reaction pH of about 7.0 and a reaction temperature of about 210° C.

In certain embodiments of the invention hemicellulose is fractionated from lignocellulosic matter by solvation with a sub-critical solvent. In the context of the present specification, a sub-critical solvent is a fluid at a temperature and pressure below its thermodynamic critical point.

In one embodiment, hemicellulose is solvated using sub-critical water. For example, sub-critical water may be used at temperature of less than about 374° C. and a pressure of less than about 22.1 MPa (221 bar). Suitable reaction temperatures and pressures may be facilitated, for example, by performing the solvation of hemicellulose in a batch reactor, a pressurized vessel or an autoclave.

In certain embodiments, the solvation of hemicellulose in sub-critical water may be performed at a reaction temperature of between about 100° C. and about 270° C. In other embodiments, the reaction temperature is between about 120° C. and about 270° C., between about 140° C. and about 270° C., between about 160° C. and about 270° C., between about 180° C. and about 270° C., between about 200° C. and about 270° C., between about 220° C. and about 270° C., between about 240° C. and about 270° C., between about 260° C. and about 270° C., between about 100° C. and about 250° C., between about 100° C. and about 230° C., between about 100° C. and about 210° C., between about 100° C. and about 190° C., between about 100° C. and about 170° C., between about 100° C. and about 150° C., or between about 100° C. and about 130° C.

Solvation of hemicellulose in sub-critical water performed at any of the above-mentioned temperatures may be performed, for example, at a pressure of less than about 22 MPa (220 bar), less than about 20 MPa (200 bar), less than about 16 MPa (160 bar), less than about 12 MPa (120 bar), less than about 8 MPa (80 bar), less than about 4 MPa (40 bar), less than about 3 MPa (30 bar), less than about 2 MPa (20 bar), or about 1 MPa (10 bar).

In one embodiment, hemicellulose is fractionated from lignocellulosic matter by solvation in sub-critical water at a temperature of about 190° C. and a pressure of about 3 MPa (30 bar).

The solvated hemicellulose component may be removed from the remaining solid matter (which substantially comprises lignin and cellulose) using any suitable means. For example, remaining solid matter comprising lignin and cellulose may be physically retained by passing the mixture through one or more appropriately sized filters through which the solvated hemicellulose fraction may pass. The solid matter may be retained on the filter(s) and washed if so desired.

Additionally or alternatively, centrifugation may be used to separate solvated hemicellulose from remaining solid matter. In a continuous system, counter current flow of solids and liquid may be used to facilitate the separation.

In certain embodiments, a hydrocyclone apparatus is used to separate the solvated hemicellulose fraction from the remaining matter comprising lignin and cellulose. A hydrocyclone is a static apparatus that applies centrifugal force to a liquid mixture so as to promote the separation of heavy components, in this case the remaining solid matter, from light components, in this case the solvated hemicellulose fraction. In general, a hydrocyclone may operate to separate hemicellulose from remaining solid matter as follows. The hydrocyclone directs inflow tangentially near the top of a vertical cylinder, converting the velocity of incoming material into a rotary motion thus creating centrifugal force. The remaining solid matter moves outward toward the wall of the cylinder where it agglomerates and spirals down the wall to an outlet. The solvated hemicellulose fraction moves toward the axis of the hydrocyclone and upwards to a different outlet.

Following hemicellulose fractionation, the remaining biomass comprising predominantly lignin and cellulose may be treated with a solvent to produce a bio-oil product using the methods of the invention.

Alternatively, the remaining biomass may be fractionated into lignin and cellulose components, either or both of which may be treated to produce a bio-oil product using the methods of the invention.

Bio-Oil Production from Cellulose and Lignin

The methods of the invention provide a means of generating a bio-oil product from material comprising lignin and cellulose using a solvent under defined reaction conditions. In general, the bio-oil product is stable. The bio-oil product may be in the form of an emulsion.

Without being limited to a particular mechanism or mode of action, it is believed that a solvent used in accordance with the methods of the invention facilitates mechanical swelling of the lignin and cellulose present in the material under treatment. This may be responsible for a number of effects including, for example, assisting "opening up" of the substrate making it more accessible and prone to hydrolysis and depolymerization. In addition, the swelling may in itself disrupt hydrogen bonds in the substrate (e.g. those present between cellulose and lignin).

For example, in the case where an aqueous alcohol (e.g. aqueous ethanol or aqueous methanol) is utilized to generate a bio-oil product in accordance with the methods of the invention, it is thought that the alcohol is able to penetrate the lignin/cellulose composite as it is less polar than water. Under certain reaction conditions water is believed to dissolve organic substances such as hydrocarbons and thus may also interact closely with the substrate to facilitate swelling. Solvation of the substrate is thought to be facilitated, at least in part, by solvent-mediated hydrolysis (e.g. base and acid catalysis). For example, hydrolysis of carbohydrates may occur predominantly through the hydrolysis of glycosidic linkages, while hydrolysis of lignin (i.e. lignin depolymerization) may be facilitated by ether linkage hydrolysis (where the ether contains at least one aromatic). In addition, it is thought that dehydration of the carbohydrates may lead to the elimination of water and formation of double bonds.

In general, the solvation of lignin is believed to arise at least in part from the cleavage of chemical bonds within the branched structure of lignin, such as ether or carbon-carbon linkages. Specific examples of linkages in the structure of lignin that may be cleaved include, but are not limited, to $\beta$-O-4 linkages (e.g. phenylpropane $\beta$-aryl ether), 5-5 linkages (e.g. biphenyl and dibenzodioxocin), $\beta$-5 linkages (e.g. phenylcoumaran), $\beta$-1 linkages (e.g. 1,2-diaryl propane), $\alpha$-O-4 linkages (e.g. phenylpropane $\alpha$-aryl ether), 4-O-5 linkages (e.g. diaryl ether) and $\beta$-$\beta$ linkages (e.g. $\beta$-$\beta$-linked structures). The solvation of cellulose is believed to arise at least in part from the chemical bonds including, for example, $\beta$-1,4-linkages between D-glucose units. Solvation may additionally involve the cleavage of bonds existing between lignin and cellulose (e.g. hydrogen bonds and ether linkages).

It is also postulated that a solvent used in accordance with the methods of the invention may act as a chemical stabilization agent. Again without being limited to a particular mechanism or mode of action, stabilization may occur through various interactions with both reaction intermediates and the bio-oil product. Chemical stabilization may be affected, for example, by alkylation, arylation, interaction with phenolic groups and/or free radical scavenging. In general, chemical stabilization serves to prevent cross-linking and polymerization, events which are believed to yield tar-like compounds. In addition, scavenging of free-radicals by the solvent (e.g. via formation of hydroxyl radicals and/or ethoxy radicals) may have the effect of converting aromatic radicals into non-radical aromatics. This in turn may reduce the potential for cross-linking involving aromatics in the bio-oil product.

In accordance with the methods of the invention, the conversion of material comprising lignin and cellulose into a bio-oil product is conducted using a solvent at elevated temperatures. Again without being bound to a particular mechanism or mode of action, it is believed that the elevated temperatures facilitate decarboxylation and elimination (dehydration) reactions whereby much of the oxygen contained in the biomass is removed as carbon dioxide gas and water, respectively.

Any material comprising lignin and cellulose may be used to perform the methods of the invention. The material may comprise any number of substances in addition to lignin and cellulose. Alternatively, the material may consist predominantly of lignin and cellulose, or consist of lignin and cellulose only.

In preferred embodiments, the material is lignocellulosic matter or is derived from lignocellulosic matter.

In alternative embodiments, the methods are used to generate bio-oil from a material comprising lignin from which cellulose has been completely or substantially removed (as may be the case after purification or fractionation of lignin from a more complex material).

In other alternative embodiments, the methods are used to generate bio-oil from a material comprising cellulose from which lignin has been completely or substantially removed (as may be the case after purification or fractionation of cellulose from a more complex material).

The methods for bio-oil production provided herein generally involve treatment of a material comprising lignin and cellulose with a solvent. When the material is lignocellulosic matter, it is contemplated that hemicellulose will first be fractionated and removed prior to generation of the bio-oil from lignin/cellulose. Preferably, the hemicellulose is fractionated and removed using the methods described above in the section entitled "Fractionation of hemicellulose".

In preferred embodiments of the invention, bio-oil is generated from material comprising lignin and cellulose matter provided in the form of a slurry. The slurry may be formed, for example, by reducing the matter into a powder of appropriate particle size (e.g. by using grinding, agitation, shredding, milling, compression/expansion and/or other types of mechanical action) and mixing with an appropriate liquid (e.g. an aqueous solvent).

In certain embodiments, the slurry is formed from solid matter comprising lignin and cellulose remaining after the fractionation of hemicellulose from lignocellulosic matter (for example, as described in the section above entitled "Fractionation of lignocellulosic matter").

The particle size of solid matter included in the slurry may be between about 10 microns and about 10,000 microns. For example, the particle size of solid matter included in the slurry may be at least about 1000, 2000, 3000, 4000, 5000, 6000, 7000, 8000 or 9000 microns. Alternatively, the particle size may be between about 10 microns and about 50 microns, between about 10 microns and about 100 microns, between about 10 microns and about 400 microns, between about 10 microns and about 500 microns, between about 100 microns and about 200 microns, between about 100 microns and about 300 microns, between about 100 microns and about 500 microns between about 100 microns and about 500 microns, or between about 100 microns and about 1000 microns.

In one embodiment, the particle size is between about 100 microns and about 400 microns.

In another embodiment, the particle size is between about 50 microns and about 500 microns.

In another embodiment, the particle size is between about 150 microns and about 300 microns.

The concentration of solid matter in the slurry may be above about 50% w/v. Alternatively, the concentration of solid matter in the slurry may be between about 1% and about 50%, between about 1% and about 40%, between about 1% and about 30%, between about 1% and about 20%, or between about 1% and about 10% w/v.

The concentration of solid matter in the slurry may be about 5%, about 10%, about 15%, about 20%, about 25% or about 30% w/v.

In certain embodiments, the concentration of solid matter in the slurry is between about 4% and about 30% w/v.

In certain embodiments, the slurry comprises between about 2% and about 45% solid matter by weight.

In certain embodiments, the slurry comprises between about 2% and about 30% solid matter by weight.

In certain embodiments, the slurry comprises about 5% solid matter by weight.

Any solvent capable of generating a bio-oil product from material comprising lignin and/or cellulose under the reaction conditions described herein may be used. The solvent may be utilised under supercritical conditions, sub-critical conditions or at conditions which oscillate above and below the thermodynamic critical point of the solvent.

In preferred embodiments, the solvent is an aqueous solvent (e.g. an aqueous acidic solution, an aqueous alkaline solution, or an aqueous solution of neutral pH (i.e. pH of about 7.0)). In the context of the present specification, an "aqueous solvent" is a solvent containing at least one percent water based on total weight of solvent. The ratio of solvent to water may be above about 0.01 (i.e. 1 part solvent: 99 parts water). Preferably, the ratio of solvent to water is equal to or above about 0.11 (i.e. 1 part solvent: 9 parts water). More preferably, the ratio of solvent to water is equal to or above about 0.25 (i.e. 1 part solvent: 4 parts water). The aqueous solvent may comprise water and between about 1% and 40% weight solvent.

In certain embodiments the solvent is an alkylating agent. The alkylating agent will, in general, comprise an alkyl chain bearing an appropriate leaving group. The transfer of an alkyl chain from the alkylating agent to the lignin/cellulose composite may facilitate solvation and/or chemical stabilization of the composite.

Non-limiting examples of suitable alkylating agents include alkylhalides, alkylsulfates, olefins, alkylphosphates, and alcohols.

Non-limiting examples of alkylhalides include methyl chloride, isopropyl chloride, ethyl bromide, and methyl iodide.

Non-limiting examples of alkylaromatics include xylenes, and trimethylbenzenes.

Non-limiting examples of suitable olefins include monoolefins such as ethylene, propylene, n-butene, isobutylene, 1-pentene, 1-hexene, cyclohexene, and 1-octene.

A non-limiting example of a suitable diolefin is 1,3-Butadiene.

Preferably, alcohol (e.g. an aqueous alcohol) is used as a solvent for the bio-oil production methods described herein. Suitable alcohols may have between about one and about ten carbon atoms. Non-limiting examples of preferred alcohols include methanol, ethanol, isopropyl alcohol, isobutyl alcohol, pentyl alcohol, hexanol and iso-hexanol.

In certain embodiments, the aqueous alcohol comprises between about 1% and about 30% alcohol by weight.

In certain embodiments, the aqueous alcohol comprises between about 5% and about 30% alcohol by weight.

In certain embodiments, the aqueous alcohol comprises about 25% alcohol by weight.

In certain embodiments, the aqueous alcohol comprises about 20% alcohol by weight.

In certain embodiments, the solvent comprises a mixture of aqueous alcohols (e.g. an aqueous mixture comprising methanol and at least one other alcohol, an aqueous mixture comprising ethanol and at least one other alcohol, an aqueous mixture comprising methanol and ethanol, or an aqueous mixture comprising methanol and ethanol and at least one other alcohol).

In certain embodiments, the solvent comprises a mixture of aqueous alcohols comprising between about 5% and about 30% alcohol by weight, comprising between about 5% and about 30% alcohol by weight, comprising about 25% alcohol by weight, or comprising about 20% alcohol by weight.

In preferred embodiments of the invention, the solvent used to produce bio-oil from material comprising lignin and/or cellulose is ethanol.

In particularly preferred embodiments, the ethanol is aqueous ethanol. The ratio of ethanol to water may be equal to or above about 0.01 (i.e. 1 part ethanol: 99 parts water). Preferably, the ratio of ethanol to water is equal to or above about 0.11 (i.e. 1 part ethanol: 9 parts water). More preferably, the ratio of ethanol to water is equal to or above about 0.25 (i.e. 1 part alcohol: 4 parts water).

In certain embodiments, the aqueous ethanol comprises between about 1% and about 30% ethanol by weight.

In certain embodiments, the aqueous ethanol comprises between about 5% and about 30% ethanol by weight.

In certain embodiments, the aqueous alcohol comprises about 25% ethanol by weight.

In certain embodiments, the aqueous alcohol comprises about 20% ethanol by weight.

Using the methods of the invention, materials comprising lignin and cellulose may be converted into a bio-oil product using a solvent (for example, any one or more of the specific alcohols, aqueous alcohols, or mixtures of aqueous alcohols referred to above) at a reaction temperature or a range of reaction temperatures of between about 200° C. and about 400° C., or between about 250° C. and about 400° C. In certain embodiments, the reaction temperature or range of reaction temperatures is between about 230° C. and about 360° C., between about 230° C. and about 350° C., between about 230° C. and about 340° C., between about 230° C. and about 330° C., between about 230° C. and about 320° C., between about 230° C. and about 310° C., between about 230° C. and about 300° C., between about 230° C. and about 290° C., between about 230° C. and about 280° C., between about 230° C. and about 270° C., between about 230° C. and about 260° C., between about 230° C. and about 250° C., between about 230° C. and about 240° C., between about 230° C. and about 350° C., between about 240° C. and about 350° C., between about 250° C. and about 350° C., between about 260° C. and about 350° C., between about 270° C. and about 350° C., between about 280° C. and about 350° C., between about 290° C. and about 350° C., between about 300° C. and about 350° C., between about 310° C. and about 350° C., between about 320° C. and about 350° C., between about 330° C. and about 350° C., or between about 340° C. and about 350° C. In certain embodiments, the reaction temperature is 320° C.

Using the methods of the invention, any of the above-mentioned reaction temperatures or ranges of reaction temperatures may be combined with a reaction pressure or a range of reaction pressures of between about 10 MPa (100 bar) and about 30 MPa (300 bar), between about 12 MPa (120 bar) and about 24 MPa (240 bar), between about 14 MPa (140 bar) and about 24 MPa (240 bar), between about 15 MPa (150 bar) and about 24 MPa (240 bar), between about 16 MPa (160 bar) and about 24 MPa (240 bar), between about 17 MPa (170 bar) and about 24 MPa (240 bar), between about 18 MPa (180 bar) and about 24 MPa (240 bar), between about 19 MPa (190 bar) and about 24 MPa (240 bar), between about 20 MPa (200 bar) and about 24 MPa (240 bar), between about 21 MPa (210 bar) and about 24 MPa (240 bar), between about 22 MPa (220 bar) and about 24 MPa (240 bar), between about 23 MPa (230 bar) and about 24 MPa (240 bar), between about 12 MPa (120 bar) and about 22 MPa (220 bar), between about 12 MPa (120 bar) and about 18 MPa (180 bar), between about 12 MPa (120 bar) and about 16 MPa (160 bar), between about 12 MPa (120 bar) and about 14 MPa (140 bar), between about 14 MPa (140 bar) and about 23 MPa (230 bar), between about 14 MPa (140 bar) and about 22 MPa (220 bar), between about 14 MPa (140 bar) and about 21 MPa (210 bar), between about 14 MPa (140 bar) and about 20 MPa (200 bar), between about 14 MPa (140 bar) and about 19 MPa (190 bar), between about 14 MPa (140 bar) and about 18 MPa (180 bar), between about 14 MPa (140 bar) and about 17 MPa (170 bar), between about 14 MPa (140 bar) and about 16 MPa (160 bar), between about 14 MPa (140 bar) and about 15 MPa (150 bar), or about 20 Mpa (200 bar).

Using the methods of the invention, conversion of matter comprising lignin and cellulose to a bio-oil may be performed using a combination of any of the above-mentioned reaction temperatures/ranges of reaction temperatures and reaction pressures/ranges of reaction pressures at a suitable reaction pH. For example, the pH may be neutral, acidic (i.e. less than 7.0) or basic (i.e. more than 7.0). In certain embodiments, the pH is between about 6.5 and 7.5.

In general, reactions to produce bio-oil in accordance with the invention are performed for a period of time sufficient to convert substantially all of the lignin and cellulose in the material, or, the majority of lignin and cellulose in the material to a bio-oil. For example, a reaction defined by any combination of the values/ranges of values of temperature, pressure and/or pH set forth above may be performed for a period of between 2 minutes and 60 minutes. In some embodiments, the reaction is performed for between about 2 minutes and about 40 minutes. In some embodiments, the reaction is performed for between about 5 minutes and about 40 minutes. In other embodiments, the reaction is performed from between about 5 minutes and about 30 minutes. In other embodiments, the reaction is performed for a period of less than about 20 minutes.

Specific reaction conditions utilized for the methods of bio-oil production provided herein will depend on factors such as the type of solvent used, whether the solvent is aqueous and if so the percentage of water in the solvent, the amount of starting material, the specific type of starting material and so on. For example, factors such as temperature and pH of the reaction mixture, isotonicity, amount of starting material, amount of solvent, and length of reaction time may be varied in order to optimize the reaction.

The solvent composition (e.g. percentage of water if aqueous) and temperature/pressure utilized during the reaction can be optimized so as to maximize the yield and/or reduce the processing time. In preferred embodiments, all or substantially all of the lignin and cellulose in a given starting material is converted into the bio-oil product.

Desired reaction conditions may be achieved, for example, by conducting the reaction in a suitable mechanical apparatus capable of maintaining increased temperature and/or increased pressure. A suitable mechanical apparatus will, in general, include any apparatus provided with suitable heating means that is designed to generate and withstand pressure.

It will be understood that a solvent used to produce a bio-oil in accordance with the methods of the invention may do so under conditions of temperature and pressure that are above the critical point of the solvent (i.e. supercritical), below the critical point of the solvent (i.e. sub-critical) and/or at the critical point of the solvent. The critical point of a solvent used in the methods will depend on factors such as the percentage of water (if an aqueous solvent is used) and the chemical state of the material under treatment. For example, the critical point of a given solvent is likely to change over the course of a given reaction as input material becomes solvated. It is also envisaged that reaction conditions in accordance with the methods of the invention may oscillate around the critical point of a substance (i.e. movement from supercritical conditions to sub-critical conditions and vice versa).

In certain embodiments, material comprising lignin and cellulose (e.g. a slurry comprising 2% to 45% solid matter by weight) is converted into a bio-oil product using aqueous alcohol as the solvent (e.g. any of the specific aqueous ethanol solvents referred to above) at a reaction temperature or a range of reaction temperatures of between about 250° C. and 400° C., and a reaction pressure or a range of reaction pressures of between about 10 MPa (100 bar) and about 25 MPa (250 bar), for a period of between about 2 minutes and about 60 minutes. Preferably, the aqueous alcohol is aqueous ethanol, Preferably, the aqueous ethanol comprises between about 1% and about 30% ethanol by weight and more preferably between about 5% and about 30% ethanol by weight. Still more preferably, the aqueous ethanol comprises about 20% or about 25% ethanol by weight.

In other embodiments, material comprising lignin and cellulose (e.g. a slurry comprising 2% to 30% solid matter by weight) is converted into a bio-oil product using aqueous ethanol comprising between about 15% and about 30% ethanol by weight, at a reaction temperature or a range of reaction temperatures of between about 280° C. and 350° C., and a reaction pressure or a range of reaction pressures of between about 15 MPa (150 bar) and about 25 MPa (250 bar), for a period of between about 5 minutes and about 30 minutes.

In further embodiments, material comprising lignin and cellulose (e.g. a slurry comprising 2% to 30% solid matter by weight) is converted into a bio-oil product using aqueous ethanol comprising between about 20% and about 25% ethanol by weight, at a reaction temperature or a range of reaction temperatures of between about 280° C. and 330° C., a reaction pressure or a range of reaction pressures of between about 18 MPa (180 bar) and about 22 MPa (220 bar), for a period of between about 5 minutes and about 20 minutes.

In other embodiments, material comprising lignin and cellulose (e.g. a slurry comprising 4% to 30% solid matter by weight) is converted into a bio-oil product using aqueous ethanol comprising between about 20% and about 25% ethanol by weight, at a reaction temperature or a range of reaction temperatures of between about 280° C. and 330° C., and a reaction pressure or a range of reaction pressures of between about 18 MPa (180 bar) and about 22 MPa (220 bar), for a period of between about 5 minutes and about 20 minutes.

In one embodiment, a bio-oil product is formed from a material comprising lignin and cellulose using aqueous ethanol (1 part ethanol: 99 parts water) at a reaction temperature of about 320° C. and a reaction pressure of about 18 MPa (180 bar).

In one embodiment, a bio-oil product is formed from a material comprising lignin and cellulose using aqueous ethanol (1 part ethanol: 9 parts water) at a reaction temperature of about 320° C. and a reaction pressure of about 18 MPa (180 bar).

In another embodiment, a bio-oil product is formed from a material comprising lignin and cellulose using aqueous ethanol (1 part ethanol: 4 parts water) at a reaction temperature of about 320° C. and a reaction pressure of about 18 MPa (180 bar).

Bio-Oil Production from Cellulose

In alternative embodiments of the invention, a bio-oil product is generated using a material comprising cellulose (i.e. cellulosic material) from which lignin has been completely or substantially removed (as may be the case after purification or fractionation of cellulose from a more complex material). Bio-oil may be generated from the material using any of the methods (including reaction conditions) described in the section above entitled "Bio-oil production from cellulose and lignin".

Lignocellulosic matter may be used to produce cellulosic material from which lignin has been completely or substantially removed.

For example, cellulosic material from which lignin has been completely or substantially removed may be obtained by fractionating lignin (and optionally hemicellulose) from lignocellulosic matter, as described in the section below entitled "Bio-oil production from lignin".

Alternatively, the cellulosic material may be generated by fractionating cellulose from lignocellulosic matter. In preferred embodiments, the fractionation is performed after an initial step of hemicellulose fractionation as described in the section above entitled "Fractionation of hemicellulose".

Fractionation of cellulose from lignocellulosic matter may be achieved using a solvent.

Examples of suitable solvents and methods by which cellulose may be solvated are described in U.S. Pat. No. 2,179,181, U.S. Pat. No. 3,447,939, U.S. Pat. No. 4,097,666, U.S. Pat. No. 4,302,252, U.S. Pat. No. 5,410,034, and U.S. Pat. No. 6,824,599.

Examples of methods by which cellulose may be solvated include hydrolytic disintegration by use of superheated steam at elevated pressure. Additionally or alternatively, cellulose may be solvated using ionic liquids, or tertiary amines.

Solvents suitable for fractionating cellulose from lignocellulosic matter or modified forms thereof (e.g. lignocellulosic matter with hemicellulose removed or substantially removed) include, but are not limited to, water, aqueous acidic solutions, aqueous alkaline solutions, and organic solvents.

Preferably, cellulose is fractionated from lignocellulosic matter or a modified form thereof using an aqueous solvent. In general, fractionation of cellulose by solvation in aqueous solution will also involve partial hydrolysis of the cellulose.

The aqueous solvent may be an aqueous acidic solvent, an aqueous basic solvent, or an aqueous solvent of neutral pH (i.e. pH of about 7.0). A suitable basic aqueous solution will have a pH of greater than about 7.0. For example, a suitable basic aqueous solvent may have a pH of between about 7.0 and about 12.0. A suitable acidic aqueous solvent may have a pH of less than about 7.0. For example, a suitable acidic aqueous solvent may have a pH of between about 7.0 and about 2.0.

The solvation of cellulose in an aqueous solvent may be performed at any suitable reaction temperature (in combination with any of the ranges or values of pH referred to above).

For example, the reaction temperature may be between about 80° C. and about 400° C. In certain embodiments of the invention, the reaction temperature is between about 100° C. and about 400° C., between about 120° C. and about 400° C., between about 140° C. and about 400° C., between about 160° C. and about 400° C., between about 180° C. and about 400° C., between about 200° C. and about 400° C., between about 220° C. and about 400° C., between about 240° C. and about 400° C., between about 260° C. and about 400° C., between about 280° C. and about 400° C., between about 300° C. and about 400° C., between about 320° C. and about 400° C., between about 340° C. and about 400° C., between about 360° C. and about 400° C., between about 380° C. and about 400° C., between about 80° C. and about 380° C., between about 80° C. and about 360° C., between about 80° C. and about 340° C., between about 80° C. and about 320° C., between about 80° C. and about 300° C., between about 80° C. and about 280° C., between about 80° C. and about 260° C., between about 80° C. and about 240° C., between about 80° C. and about 220° C., between about 80° C. and about 200° C., between about 80° C. and about 180° C., between about 80° C. and about 160° C., between about 80° C. and about 140° C., between about 80° C. and about 120° C., between about 80° C. and about 100° C., or between about 80° C. and about 90° C.

In one embodiment, the cellulose is solvated and partially hydrolysed using water at a pH of about 7.0 and a reaction temperature of about 340° C.

The solvation of cellulose in aqueous solution may be performed at any reaction pressure (in combination with any of the ranges or values of reaction temperature and/or reaction pH referred to above).

For example, the solvation of cellulose in aqueous solution may be performed at a reaction pressure of between about 0.01 MPa (0.1 bar) and about 25 MPa (250 bar), between about 0.01 MPa (0.1 bar) and about 10 MPa (100 bar), between about 0.01 MPa (0.1 bar) and about 5 MPa (50 bar), preferably between about 0.02 MPa (0.2 bar) and about 5 MPa (50 bar) and more preferably between about 1 MPa (10 bar) and about 4 MPa (40 bar).

In general, reactions are performed for a period of time sufficient to solvate (i.e. fractionate) substantially all of the cellulose, or, the majority of cellulose.

For example, a reaction under conditions defined by a combination of any of the values or ranges of reaction pH and/or reaction temperature and/or reaction pressure referred to above may be performed for less than 20 minutes. In some embodiments, the reaction is performed for between about 2 minutes and about 20 minutes. In other embodiments, the reaction is performed from between about 5 minutes and about 15 minutes. In other embodiments, the reaction is performed for a period of more than 20 minutes.

Optimal reaction conditions for the solvation of cellulose will ultimately depend on factors including the purity of the cellulose type under treatment and the specific solvent used. For example, factors such as temperature and pH of the reaction mixture, isotonicity, amount of cellulosic matter and solvent, and length of reaction time may be varied in order to optimise the reaction.

Optimal reaction conditions will be readily apparent to the skilled addressee upon analysis of the solvated cellulose, which may be performed using standard methods generally known in the art. For example, solvated cellulose may be analysed using spectroscopy techniques. Suitable spectroscopy techniques include, but are not limited to, near infra red spectroscopy, fourier transform infrared spectroscopy, nuclear magnetic resonance spectroscopy, raman microscopy, UV microspectrophotometry and X-ray diffraction. Additionally or alternatively, solubilized cellulose may quantified by high performance liquid chromatography.

In certain embodiments, the fractionation of cellulose from lignocellulosic matter may be achieved by treatment with supercritical water. In general, water may be brought into a supercritical state by heating to above a temperature of about 370° C. under pressure of about 22.0 MPa (220 bar).

Supercritical conditions may be achieved, for example, by conducting the reaction in a suitable mechanical apparatus capable of maintaining increased temperature and/or increased pressure. Examples of a suitable mechanical apparatus include an autoclave, a supercritical reactor, or any apparatus provided with suitable heating means and designed to withstand the pressures utilized. In general, the apparatus will preferably provide a means of mixing a solvent with the material comprising cellulose and bringing/maintaining the solvent in the mixture to a supercritical state.

Cellulosic material from which lignin has been completely or substantially removed may be further treated or modified prior to conversion to a bio-oil using the methods of the invention. This may be done to assist or enhance the chemical or physical characteristics of the cellulose-containing material such that it is better suited for oil conversion using the methods described herein.

Bio-Oil Production from Lignin

In alternative embodiments of the invention, a bio-oil product is generated using a material comprising lignin from which cellulose has been completely or substantially removed (as may be the case after purification or fractionation of lignin from a more complex material). Bio-oil may be generated from the material using any of the methods (including reaction conditions) described in the section above entitled "Bio-oil production from cellulose and lignin".

Material comprising lignin from which cellulose has been completely or substantially removed may be obtained by fractionating cellulose (and optionally hemicellulose) from lignocellulosic matter, as described in the section below above "Bio-oil production from cellulose".

Alternatively, the material may be generated by fractionating lignin from lignocellulosic matter. In preferred embodiments, the fractionation is performed after an initial step of hemicellulose fractionation as described in the section above entitled "Fractionation of hemicellulose".

Fractionation of lignin from lignocellulosic matter may be achieved, for example, by treatment with a supercritical solvent. In preferred embodiments, the fractionation is performed after an initial step of hemicellulose fractionation as described in the section above entitled "Fractionation of hemicellulose".

In general, a supercritical solvent is a solvent heated above its critical temperature and pressurized above its critical pressure such that it exhibits properties of both a gas and a liquid. However, it will be understood that the term "supercritical" as used herein also encompasses conditions of temperature and/or pressure that are a small, although not substantial, amount (e.g. approximately 5%) below the supercritical point of the substance in question (i.e. "sub-critical"). Accordingly, the term "supercritical" also encompasses oscillatory behaviour around the supercritical point of a substance (i.e. movement from supercritical conditions to sub-critical conditions and vice versa).

Any supercritical solvent may be used that is capable of solvating lignin from biomass. Non-limiting examples of suitable solvents include nitrous oxide, sulfur dioxide, ammonia based solvents, amines, carbon dioxide, and mixtures thereof.

Fractionation of lignin with a supercritical solvent may be performed at a temperature that is at least the critical temperature for the solvent selected, and preferably, above the critical temperature. When such operating temperatures are contemplated, the pressure applied during the reaction will be at least equivalent to that required to maintain the solvent as a supercritical fluid. Temperature, solvent composition, and pressure range during the solvation of lignin can be selected so as to maximize lignin fractionation as well as to decrease processing time. Examples of supercritical temperatures and pressures for various solvents suitable for the solvation of lignin are provided in Table 1 below,

TABLE 1 non-limiting examples of various supercritical solvents that may be utilised to solvate lignin from lignocellulosic matter (or a modified form thereof with hemicellulose removed)

| Solvent | Molecular weight g/mol | Critical temperature K | Critical pressure MPa (atm) | Critical density g/cm$^3$ |
|---|---|---|---|---|
| Carbon dioxide ($CO_2$) | 44.01 | 304.1 | 7.38 (72.8) | 0.469 |
| Water ($H_2O$) | 18.02 | 647.3 | 22.12 (218.3) | 0.348 |
| Methane ($CH_4$) | 16.04 | 190.4 | 4.60 (45.4) | 0.162 |
| Ethane ($C_2H_6$) | 30.07 | 305.3 | 4.87 (48.1) | 0.203 |
| Propane ($C_3H_8$) | 44.09 | 369.8 | 4.25 (41.9) | 0.217 |
| Ethylene ($C_2H_4$) | 28.05 | 282.4 | 5.04 (49.7) | 0.215 |
| Propylene ($C_3H_6$) | 42.08 | 364.9 | 4.60 (45.4) | 0.232 |
| Methanol ($CH_3OH$) | 32.04 | 512.6 | 8.09 (79.8) | 0.272 |
| Ethanol ($C_2H_5OH$) | 46.07 | 513.9 | 6.14 (60.6) | 0.276 |

Supercritical conditions may be achieved, for example, by conducting the reaction in a suitable mechanical apparatus capable of maintaining increased temperature and/or increased pressure. Examples of a suitable mechanical apparatus include an autoclave, a supercritical reactor, or any apparatus provided with suitable heating means and that is designed to withstand the pressures utilized. In general, the apparatus will preferably provide a means of mixing a solvent with the material comprising lignin and bringing/maintaining the solvent in the mixture to a supercritical state.

In one embodiment of the invention, a supercritical alcohol is used to solvate the lignin component. Examples of suitable alcohols include, but are not limited to, methanol, ethanol, isopropyl alcohol, isobutyl alcohol, pentyl alcohol, hexanol and iso-hexanol.

In a preferred embodiment, lignin is fractionated from biomass using supercritical ethanol. In general, ethanol may be brought into a supercritical state by heating the reaction above a temperature of above about 245° C. under pressure of above about 6.0 MPa (60 bar).

In certain embodiments, lignin is separated from solid matter remaining after fractionation of hemicellulose from lignocellulosic matter. The separation of lignin is performed using supercritical ethanol as a solvent at a reaction temperature of above about 230° C. and a pressure of above about 5.5 MPa (55 bar). Preferably, the reaction is performed at a reaction temperature of above about 250° C. and a pressure of above about 6.5 MPa (65 bar). In certain embodiments, the reaction is performed for between about 2 minutes and about 15 minutes. Preferably the reaction is performed for between about 3 minutes and about 10 minutes.

The solvated lignin fraction may be removed from remaining solid matter, for example, by using cyclone apparatus. A cyclone apparatus may operate to separate lignin from remaining solid matter as follows. A high speed rotating air-flow comprising solvated lignin may be established within a conical or cylindrical cyclone, the air flowing in a spiral pattern from an upper (wider) end to a lower (narrower) end. The air flow exits the cyclone in a straight stream through the center of the cyclone and out the upper portion. Particles of remaining solid matter in the rotating air stream have too much inertia to remain in the air stream, and fall to the bottom of lower end of the cyclone where they are removed.

Material comprising lignin from which cellulose has been completely or substantially removed may be further treated or modified prior to conversion to oil using the methods described herein. This may be done to assist or enhance the chemical or physical characteristics of the lignin-containing material such that it is better suited for oil conversion using the methods described herein.

Bio-Oil Product

Certain embodiments of the invention relate to a bio-oil product obtained or obtainable by the methods of the invention. The bio-oil product will, in general, be a stable bio-oil product.

The bio-oil product may comprise compounds including, but not limited to, linear and branched aliphatics and aromatics with and without functional groups (e.g. hexane, toluene), methoxyphenol, ethylmethoxyphenol and methoxypropenylphenol. Compounds within the bio-oil may comprise functional groups including, but not limited to, phenols (e.g. ArOH), aldehydes (e.g. RCHO), aromatic groups, alkylating groups (e.g. olefin), oxygen-containing functional groups (e.g. alcohols, ethers, aldehydes, ketones, and carboxylic acids), methyl, methylene and aromatic methyl.

The bio-oil product may be produced in the form of an emulsion. Non-limiting examples of compounds that may be present in the emulsion include phenol, 2-cyclopentene-1-one, 2-methyl, methoxyphenol, ethylmethoxyphenol, and methoxypropylphenol.

In certain embodiments, the emulsion comprises a lighter aqueous phase and heavier black oil phase.

The lighter aqueous phase may comprise compounds including, but not limited to, Ether,1-propenylpropyl, 2-Cyclopenten-1-one, 2-methyl-, Phenol, Phenol, 2-methoxy-, 2,3-Dimethylhydroquinone, Phenol, 4-ethyl-2-methoxy-, 1,2-Benzenediol, 4-methyl-, Phenol, 2-methoxy-4-propyl-, Vanillin, and Phenol, 2-methoxy-.

The heavier black oil phase may comprise about 70%-80% carbon, and about 5%-10% hydrogen. The black oil phase may comprise compounds including, but not limited to, Phenol, 4-ethyl-2-methoxy-, Phenol, 2-methoxy-4-propyl-, Oleic Acid, 2-Isopropyl-10-methylphenanthrene, 3-(3-Hydroxy-4-methoxyphenyl)-1-alanine, (−)-Nortrachelogenin, 7-(3,4-Methylenedioxy)-tetrahydrobenzofuranone, 1-Phenanthrenecarboxylic acid, 1,2,3,4,4a,9,10,10a-octahydro-1,4a-dimethyl-7-(1-methylethyl)-, methyl ester, [1R-(1.alpha, 4a.beta.,10a.alpha)], 1-Phenanthrenecarboxylic acid, 1,2,3,4,4a,9,10,10a-octahydro-1,4a-dimethyl-7-(1-methylethyl)-, [1R-(1.alpha., 4a.beta.,10a.alpha)], and Carinol.

The bio-oil phase may be separated from the emulsion using standard techniques known in the art, examples of which include the use of high temperatures, pressure, gravity, microfiltration, chemicals (e.g. such as extractants and demulsifiers), high shear, and sonic energy. Specific examples of methods by which oil may be separated from the emulsion include the use of high shear or turbulence to drive the oil from the mixture (see for example, U.S. Pat. No. 4,481,130), devices such as those described in U.S. Pat. No. 5,538,628 and U.S. Pat. No. 4,483,695, and processes such as those described in PCT publication No. WO 2001/074468.

Preferably, the bio-oil product has an energy content of between about 10 MJ/kg and about 30 MJ/Kg. In certain embodiments, the bio-oil product has an energy content of between about 10 MJ/kg and about 25MJ/Kg, between about 18 MJ/kg and about 28MJ/Kg, or between about 10 MJ/kg and about 15MJ/Kg. In specific embodiments, the bio-oil product has an energy content of about 30 MJ/Kg.

The bio-oil product may be used in any number of applications. In certain embodiments, the bio-oil is used as a biofuel. The bio-oil product may be used directly. Additionally or alternatively, the bio-oil may be used as a fuel additive. For example, the bio-oil product may be blended with other fuels, including for example, ethanol, biodiesel and the like. Additionally or alternatively, the bio-oil product may be further processed, for example, for conversion into another fuel.

Saccharification and Fermentation of Hemicellulose

Fractionated hemicellulose obtained in accordance with the methods described of the invention may be subjected to saccharification to produce fermentable sugars. For example, saccharification of fractionated hemicellulose may produce polysaccharides, oligosaccharides, disaccharides, monosaccharides or mixtures thereof. Preferably, saccharification of the hemicellulose component will produce polysaccharide chains comprising between about two and about 50 monosaccharide units. More preferably, saccharification of the hemicellulose component will produce polysaccharide chains comprising between about two and about 10 monosaccharide units, and/or between about five monosaccharide units and about two monosaccharide units. Most preferably, saccharification of the hemicellulose component will produce monosaccharides.

Production of shorter polysaccharide chains, oligosaccharides, disaccharides and/or monosaccharides may be achieved by the cleavage of one or more chemical bonds present in fractionated hemicellulose using any suitable means. Non-limiting examples of preferred bonds within the structure of hemicellulose that may be cleaved include S-glycosidic bonds, N-glycosidic bonds, C-glycosidic bonds, O-glycosidic bonds, α-glycosidic bonds, β-glycosidic bonds, 1,2-glycosidic bonds, 1,3-glycosidic bonds, 1,4-glycosidic bonds and 1,6-glycosidic bonds, ether bonds, hydrogen bonds and/or ester bonds.

Saccharification of fractionated hemicellulose may be performed using any suitable method known in the art.

For example, pyrolysis may be used to cleave chemical bonds in fractionated hemicellulose to produce shorter polysaccharides, oligosaccharides, disaccharides, monosaccharides or mixtures thereof. In general, pyrolysis involves cleavage of chemical bonds by the application of heat. Non-limiting examples of pyrolysis techniques that may be utilized for saccharification include anhydrous pyrolysis (performed in the absence of oxygen), hydrous pyrolysis (performed in the presence of water) and vacuum pyrolysis (performed in a vacuum). Methods by which heat may be provided for pyrolysis are generally known in the art and include, for example, direct heat transfer using a hot gas or circulating solids and indirect heat transfer with exchange surfaces such as walls or tubes. Suitable reactors for pyrolysis are described, for example, in U.S. Pat. No. 3,853,498, U.S. Pat. No. 4,510,021, Scott et al., *Canadian Journal of Chemical Engineering* (1984) 62: 404-412 and Scott et al., *Industrial and Engineering Chemistry Process and Development* (1985) 24: 581-588.

Additionally or alternatively, saccharification of fractionated hemicellulose may be achieved by hydrolysis. For example, fractionated hemicellulose may be hydrolyzed by the addition of a dilute acid (e.g. sulfuric acid), a dilute base, or pH neutral water with the application of heat.

Hemicellulose fractionated from lignocellulosic matter may be hydrolyzed using one or more hydrolytic enzymes. Any enzyme capable of catalyzing the hydrolysis of hemicellulose to produce shorter polysaccharides, oligosaccharides, disaccharides, monosaccharides and mixtures thereof may be used. In general, hydrolytic enzymes suitable for saccharification of hemicellulose fractionated using the methods of the invention are those classified under EC 3 (hydrolases) of the enzyme nomenclature of the Nomenclature Committee of the International Union of Biochemistry and Molecular Biology (NC-IUBMB) (http://www.chem.qmul.ac.uk/iubmb/)

nomenclature as of the filing date of this application. Preferably, the hydrolytic enzymes utilized are those classified under class EC 3.2 (glycosylases) of the NC-IUBMB enzyme nomenclature.

In certain embodiments, hydrolytic enzymes suitable for use in the methods described herein are those classified under subclass 3.2.1 (Glycosidases, i.e. enzymes hydrolyzing O- and S-glycosyl compounds) of the NC-IUBMB nomenclature. In other embodiments, hydrolytic enzymes that may be utilized are those classified under subclass EC 3.2.2 (Hydrolyzing N-Glycosyl Compounds) of the NC-IUBMB nomenclature. In other embodiments, hydrolytic enzymes that may be utilized are those classified under subclass EC 3.2.3 (Hydrolyzing S-Glycosyl Compounds) of the NC-IUBMB nomenclature.

Non-limiting examples of glycoside hydrolases and carbohydrases suitable for use in the methods described herein and commercial sources of those enzymes are described in US Patent Publication No. 20060073193. Preferred examples include cellulases, xylanases, arabinosidases, β-glucosidases, β-xylosidases, mannanases, galactanases, dextranases, endoglucanases, and alpha-galactosidase.

Hydrolytic enzymes may be applied in a purified or substantially purified form to the fractionated hemicellulose, or in combination with other substances or compounds (e.g. as part of a culture supernatant). Additionally or alternatively, a hydrolytic enzyme-producing microorganism or mixtures of microorganisms capable of producing hydrolytic enzymes may be cultured in the presence of hemicellulose fractionated in accordance with the methods described herein to provide a source of hydrolytic enzymes.

Hydrolytic enzymes suitable for use in accordance with the methods described herein may be derived from any suitable microorganism, including but not limited to, bacteria and fungi/yeast. The microorganism may be a psychrophilic, mesophilic, thermophilic or extremely thermophilic organism, in accordance with the classification described in Brock, 1986, "*Thermophiles: General Molecular and Applied Microbiology*", (T. D Brock, Ed) John Wiley and Sons, Inc. New York, and Bergquist et al., 1987, Biotechnol Genet. Eng. Rev. 5:199-244.

In one embodiment, enzymatic hydrolysis of fractionated hemicellulose is performed using thermophilic hydrolytic enzymes. The use of thermostable hydrolytic enzymes for the hydrolysis of fractionated hemicellulose offers several advantages over the use of hydrolytic enzymes that operate optimally at lower temperatures, including higher specific activity and higher stability. Typically, thermophilic hydrolytic enzymes display hydrolytic activity at elevated reaction temperatures. For example, a thermophilic hydrolytic enzyme will typically remain active at a reaction temperature of more than 60° C.

Non-limiting examples of bacteria from which suitable hydrolytic enzymes may be derived include *Acidothermus* sp. (e.g. *A. cellulolyticus*), *Anaerocellum* sp. (e.g. *A. thermophilum*), *Bacillus* sp., *Butyrivibrio* sp. (e.g. *B. fibrisolvens*), *Cellulomonas* sp. (e.g. *C. fimi*), *Clostridium* sp. (e.g. *C. thermocellum, C. stercorarium*), *Erwinia* sp. (e.g. *E. chrysanthemi*), *Fibrobacter* sp. (e.g. *F. succinogenes*), *Micromonospora* sp., *Rhodothermus* sp. (e.g. *R. marinus*), *Ruminococcus* sp. (e.g. *R. albus, R. flavefaciens*), *Streptomyces* sp., *Thermotoga* sp. (e.g. *T. maritima, T. neapolitana*), *Xanthomonas* sp. (e.g. *X. campestris*) and *Zymomonas* sp. (e.g. *Z. mobilis*).

Non-limiting examples of fungi/yeast from which suitable hydrolytic enzymes may be derived include *Aureobasidium* sp., *Aspergillus* sp. (e.g. *A. awamori, A. niger* and *A. oryzae*), *Candida* sp., *Chaetomium* sp. (e.g. *C. thermophilum, C. thermophila*), *Chrysosporium* sp. (e.g. *C. lucknowense*), *Corynascus* sp. (e.g. *C. thermophilus*), *Dictyoglomus* sp. (e.g. *D. thermophilum*), *Emericella* sp., *Fusarium* sp., *Gliocladium* sp., *Hansenula* sp., *Humicola* sp. (e.g. *H. insolens* and *H. grisea*), *Hypocrea* sp., *Kluyveromyces* sp., *Myceliophthera* sp. (e.g. *M. thermophila*), *Neurospora* sp., *Penicillium* sp., *Pichia* sp., *Rhizomucor* sp. (e.g. *R. pusillus*), *Saccharomyces* sp., *Schizosaccharomyces* sp., *Sporotrichum* sp., *Thermoanaerobacterium* sp. (e.g. *T. saccharolyticum*), *Thermoascus* sp. (e.g. *T. aurantiacus, T. lanuginosa*), *Thermomyces* sp. (e.g. *T. lanuginosa*), *Thermonospora* sp. (e.g. *T. curvata, T. fusca*), *Thielavia* sp. (e.g. *T. terrestris*), *Trichoderma* sp. (e.g. *T. reesei, T. viride, T. koningii, T. harzianum*), and *Yarrowia* sp.

Suitable microorganisms that naturally produce hydrolytic enzymes, for example any of the bacteria or fungi/yeasts referred to above, may be cultured under suitable conditions for propagation and/or expression of the hydrolytic enzyme or enzymes of interest. Methods and conditions suitable for the culture of microorganisms are generally known in the art and are described in, for example, *Current Protocols in Microbiology* (Coico et al. (Eds), John Wiley and Sons, Inc, 2007).

Recombinant organisms may be used as a source of hydrolytic enzymes for saccharification of hemicellulose fractionated in accordance with the methods described herein. Additionally or alternatively, recombinant organisms capable of producing hydrolytic enzymes may be cultured with fractionated hemicellulose. Recombinant microorganisms including bacterial or fungal/yeast strains expressing one or more hydrolytic enzymes derived from an exogenous source may be generated. Methods for the production of recombinant microorganisms are generally known in the art and are described, for example, in Ausubel et al., (Eds) *Current Protocols in Molecular Biology* (2007) John Wiley & Sons; Sambrook et al., *Molecular Cloning: A Laboratory Manual*, (2000) 3rd Ed., Cold Spring Harbor Laboratory Press; *Molecular Cloning* (Maniatis et al., Cold Spring Harbor Laboratory, Cold Spring Harbor, N.Y., 1982); and *Current Protocols in Microbiology* (Coico et al. (Eds), John Wiley and Sons, Inc, 2007).

The reaction conditions for enzymatic hydrolysis are typically based on consideration of the conditions suitable for the specific enzyme or mixture of enzymes. In general, typical conditions for enzymatic hydrolysis include a reaction temperature of between about 30° C. and about 90° C., and a pH of between about 4.0 and about 8.0. Suitable reaction temperatures and pH for enzymatic hydrolysis of polysaccharides are described, for example, in Viikari et al., "*Thermostable Enzymes in Lignocellulosic Hydrolysis*", 2007, 108: 121-145.

Non-limiting examples of oligosaccharide fragments that may be produced by saccharification of hemicellulose include oligosaccharides such as mannan-oligosaccharides, fructo-oligosaccharides and galacto-oligosaccharides.

Non-limiting examples of disaccharide fragments that may be produced by saccharification of hemicellulose include sucrose, lactose, maltose, trehalose, cellobiose, laminaribiose, xylobiose, gentiobiose, isomaltose, mannobiose, kojibiose, rutinose, nigerose, and melibiose.

Non-limiting examples of monosaccharide fragments that may be produced by saccharification of hemicellulose include trioses including aldotrioses (e.g. glyceraldehyde) and ketotrioses (e.g. dihydroxyacetone), tetroses including aldotetroses (e.g. threose and erythrose) and ketotetroses (e.g. erythrulose), pentoses including aldopentoses (e.g. lyxose, ribose, arabinose, deoxyribose) and ketopentoses (e.g. xylulose and ribulose), hexoses including aldohexoses (e.g. glucose, mannose, altrose, idose, galactose, allose, talsoe and gulose) and ketohexoses (e.g. fructose, psicose, tagatose and sorbose), heptoses including keto-heptoses (e.g. sedoheptulose and mannoheptulose), octoses including octolose and 2-keto-3-deoxy-manno-octonate and nonoses including sialose.

In a preferred embodiment, saccharification of the hemicellulose fractions yields an aqueous solution comprising shorter length polysaccharide chains, oligosaccharides, disaccharides, monosaccharides, or mixtures thereof.

In an alternative embodiment of the invention, fractionated hemicellulose obtained in accordance with the methods described herein may be subjected to hydrothermal upgrading in sub-supercritical water to produce fermentable sugars. Methods for hydrothermal upgrading are known in the art and are described for example in Srokol et al., "*Hydrothermal upgrading of biomass to biofuel; studies on some monosaccharide model compounds*" Carbohydr Res. 2004 Jul. 12; 339(10):1717-26.

Certain embodiments of the invention relate to saccharides obtainable or obtained from fractionated hemicellulose in accordance with the methods described herein.

In accordance with the methods described herein, sugars derived from fractionated hemicellulose may be fermented to produce one or more fermented sugar products. For example, the microorganism may be capable of converting saccharide fragments into alcohols (e.g. ethanol), or organic acids (for example succinic acid and glutamic acid). The organic acids may be used in the production of other products, for example biopolymers, amino acids and antibiotics. Suitable microorganisms for fermentation include, but are not limited to, bacteria, fungi/yeast, and/or recombinant varieties of those organisms.

Fermentation may be performed directly on fractionated hemicellulose. Additionally or alternatively, fermentation may be performed on fragmented saccharides derived from saccharification of the fractionated hemicellulose. Additionally or alternatively, fermentation may be performed simultaneously with saccharification of fractionated hemicellulose. For example, a reaction mixture comprising hydrolytic enzymes and/or microorganisms capable of producing hydrolytic enzymes may be combined with microorganisms that ferment sugars and applied under suitable culture conditions to hemicellulose fractionated in accordance with the methods described herein.

In certain embodiments, residual lignin may be removed from the fractionated hemicellulose components prior to fermentation. Residual lignin may be removed, for example, using methods described in Mosier et al., "*Features of promising technologies for pretreatment of lignocellulosic biomass*", 2005, Bioresource Technology, 96:673-86.

In general, fermentation may be performed using any microorganism capable of converting saccharides into one or more desired fermented sugar products. For example, the microorganism may be capable of converting saccharides into alcohols (including ethanol), or organic acids (for example succinic acid and glutamic acid). The organic acids may be used in the production of other fermented sugar products, for example biopolymers, amino acids and antibiotics.

In certain embodiments, the microorganism is capable of fermenting saccharides derived from fractionated hemicellulose into one or more alcohols. Non-limiting examples of alcohols that may be produced in accordance with the methods described herein include xylitol, mannitol, arabinol, butanol and ethanol.

In a preferred embodiment, 5-carbon saccharides (pentoses) derived from saccharification of the hemicellulose fraction are fermented to produce alcohols, non-limiting examples of which include xylitol, mannitol, arbinol and ethanol.

Non-limiting examples of microorganisms capable of producing ethanol from saccharides include *Zymomonas* sp. (e.g. *Z. mobilis*), *Saccharomyces* sp. (e.g. *S. cerevisiae*), *Candida* sp. (e.g. *C. shehatae*), *Schizosaccharomyces* sp. (e.g. *S. pombe*), *Pachysolen* sp. (e.g. *P. tannophilus*), and *Pichia* sp. (e.g. *P. stipitis*).

Microorganisms suitable for the fermentation of saccharides to produce mannitol include, for example, fungi/yeast and lactic acid bacteria. Suitable microorganisms will in general express enzymes necessary for mannitol production, for example, mannitol dehydrogenase.

Examples of bacterial species that may be used for the fermentation of saccharides to mannitol include *Leuconostoc* sp. (e.g. *Leuconostoc mesenteroides*), *Lactobacillus* sp. (e.g. *L. bevis, L. buchnei, L. fermeyitum, L. sanfranciscensis*), *Oenococcus* sp. (e.g. *O. oeni*), *Leuconostoc* sp. (e.g. *L. mesenteriode*) and *Mycobacterium* sp. (e.g. *M. smegmatis*).

Examples of fungi/yeast suitable for the fermentation of saccharides to produce mannitol include, but are not limited to, *Basidiomycetes* sp., *Trichocladium* sp., *Geotrichum* sp., *Fusarium* sp., *Mucor* sp. (e.g. *M. rouxii*), *Aspergillus* sp. (e.g. *A. nidulans*), *Penicillium* sp. (e.g. *P. scabrosum*), *Candida* sp. (e.g. *C. zeylannoide, C. lipolitica*), *Cryptococcus* sp. (e.g. *C. neoformans*) and *Torulopsis* sp. (e.g. *T. mannitofaciens*).

Methods for the fermentation of saccharides to produce mannitol are described, for example, in U.S. Pat. No. 6,528, 290 and PCT publication No. WO/2006/044608.

Microorganisms suitable for the fermentation of saccharides to produce xylitol include yeasts such as *Saccharomyces Candida* sp. (e.g. *C. magnoliae, C. tropicalis, C. guilliermondif*), *Pichia* sp., and *Debaryomyces* sp. (e.g. *D. hansenii*). Methods for the fermentation of xylitol from saccharides are described, for example, in U.S. Pat. No. 5,081,026, U.S. Pat. No. 5,686,277, U.S. Pat. No. 5,998,181, and U.S. Pat. No. 6,893,849.

In preferred embodiments of the invention, fermentation of saccharides is performed using one or more recombinant microorganisms. Methods for the production of recombinant microorganisms are generally known in the art and are described, for example, in Ausubel et al., (Eds) *Current Protocols in Molecular Biology* (2007) John Wiley & Sons and Sambrook et al., *Molecular Cloning: A Laboratory Manual*, (2000) 3rd Ed., Cold Spring Harbor Laboratory Press, Cold Spring Harbor, N.Y. In general, recombinant microorganisms suitable for use in the methods described herein will express one or more genes encoding enzymes necessary for the conversion of saccharides to the desired target product.

Examples of preferred recombinant ethanologenic microorganisms are those which express alcohol dehydrogenase and pyruvate decarboxylase. Genes encoding alcohol dehydrogenase and pyruvate decarboxylase may be obtained, for example, from *Zymomonas mobilis*. Examples of recombinant microorganisms expressing one or both of these enzymes and methods for their generation are described, for example, in U.S. Pat. No. 5,000,000, U.S. Pat. No. 5,028,539, U.S. Pat. No. 424,202, and U.S. Pat. No. 5,482,846.

Suitable recombinant microorganisms may be capable of converting both pentoses and hexoses to ethanol. Recombinant microorganisms capable of converting pentoses and hexoses to ethanol are described, for example, in U.S. Pat. No. 5,000,000, U.S. Pat. No. 5,028,539, U.S. Pat. No. 5,424,202, U.S. Pat. No. 5,482,846, and U.S. Pat. No. 5,514,583.

Culture conditions suitable for the fermentation of saccharides to alcohols, organic acids and other fermented sugar products are generally known in the art, and are described in, for example, Bonifacino et al., (Eds) *Current Protocols in Cell Biology* (2007) John Wiley and Sons, Inc. and Coico et al., (Eds) *Current Protocols in Microbiology* (2007) John Wiley and Sons, Inc. Generally, microorganisms may be cultured at a temperature of between about 30° C. and about 40° C., and a pH of between about 5.0 and about 7.0. In may be advantageous to add cofactors for the fermenting enzymes and/or nutrients for the microorganisms to optimize the enzymatic fermentation. For example, cofactors such as NADPH and/or NAD may be added to the culture to assist the activity of fermenting enzymes (e.g. xylose reductase and xylitol dehydrogenase). Carbon, nitrogen and sulfur sources may also be included in the culture.

Fermented sugar products derived from fractionated hemicellulose may be further refined or processed.

Accordingly, certain embodiments of the invention relate to fermented sugar products obtained or obtainable from fractionated hemicellulose produced in accordance with the methods described herein.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

EXAMPLES

The invention will now be described with reference to specific examples, which should not be construed as in any way limiting.

Example 1

Overview

Figure 6:
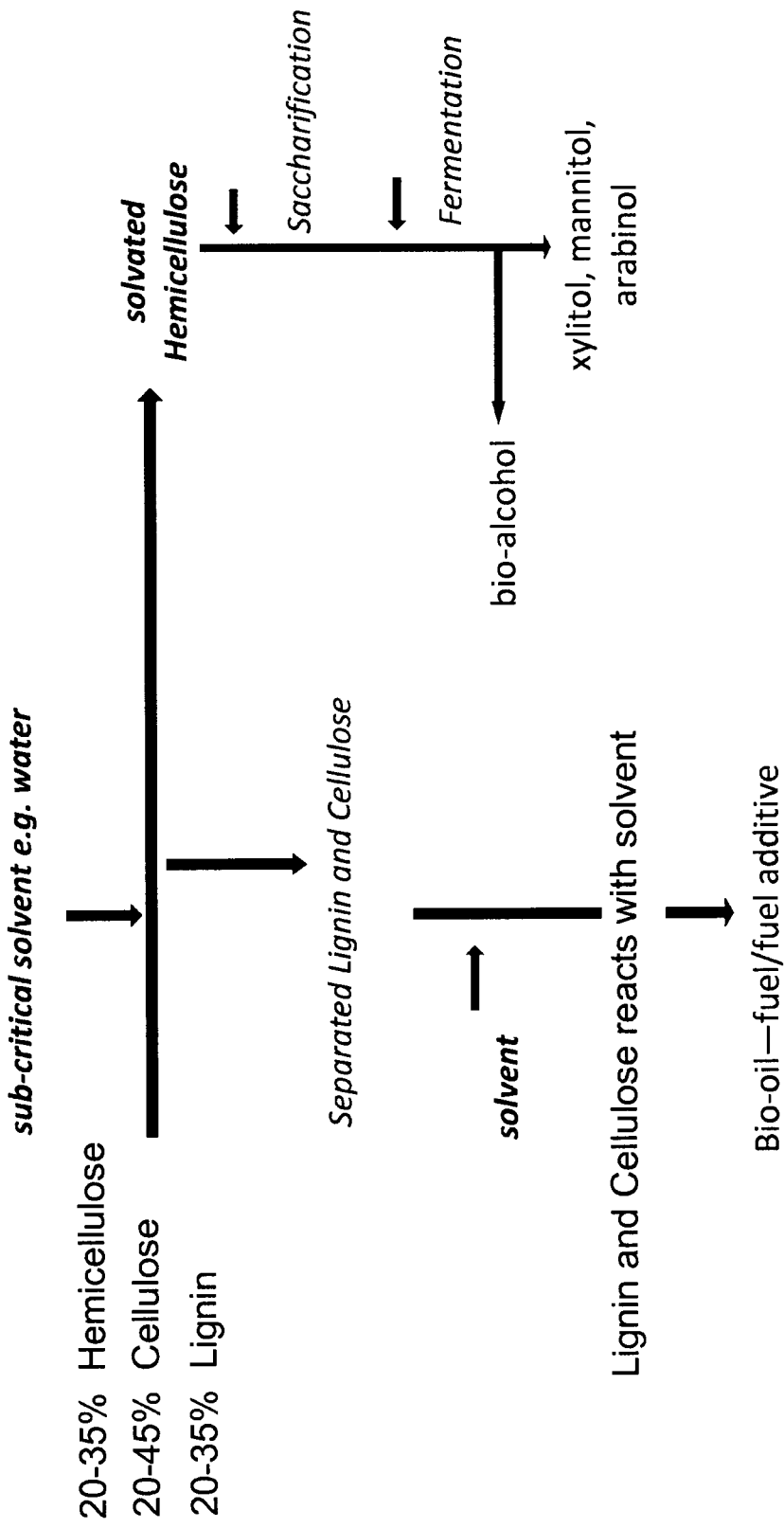

A flow diagram illustrating certain embodiments of the invention is provided in FIG. 6.

Example 2

Extraction of Hemicellulose from Wood Flour Wood Flour Slurry Preparation

A measured amount of water was added to a feed tank using a flow indicator. Wood flour was added to the tank and a stirrer used to suspend the wood flour and form a slurry.

The slurry was fed into the plant reactor via a variable speed positive displacement pump. The speed of the pump was set to provide the required production rate. The pump may be fed with either wood flour slurry or town water for startup and shutdown purposes via the automatic three way valve.

A pressure relief valve fitted to the discharge of the slurry feed pump limited the maximum system pressure to 60 bar. The discharge pressure was monitored by an online pressure transmitter. The feed tank may be drained and flushed by diverting the discharge of the feed pump to drain via a three way manual valve.

Heating

The slurry was heated in two stages, first using double or concentric pipe heat exchanger banks supplied with saturated steam from a boiler and subsequently with electric heating elements.

In the first heating stage the slurry was raised close to the temperature of saturated steam (180° C.) fed directly from the boiler at full pressure. The temperature exiting this heating state was monitored by an online temperature transmitter. The steam condensate from the first heating stage was returned to the boiler water feed tank via steam traps. This increased the thermal efficiency of the boiler and enabled a greater rate of steam generation.

Upon exiting the steam heating stage, the slurry made its way past three 4 kW electric 3 m long heating elements clamped in series to the process tubing. This long heating path (9 m) gradually heated the slurry to the final target temperature (210° C.). The final temperature of the slurry was monitored by an online temperature transmitter, and was controlled by varying the supply voltage to all three heating elements.

The heating stages were arranged to enable a slow and gradual heating of the slurry to the target temperature of 210° C., to avoid the risk of thermally decomposing any material and leading to process blockages.

Reaction

Following heating to the target temperature, the slurry was retained in a series of larger diameter pipes (50 mm) for 5 minutes to provide sufficient time for the reaction to occur. Residence time in the reactor can be reduced to 2.5 minutes (if desired) by reconfiguring the reactor piping. These reaction pipes were well insulated but not heated, and the exit temperature was monitored by an online temperature transmitter. The plant was preheated prior to operation by running on water until the target conditions were reached.

Cooling

Upon exiting the reactor, the slurry was cooled to approximately 80° C. using a bank of concentric pipe heat exchangers and town water. Cooling to that temperature was required for operation of the vacuum filter, due to the high vapour pressure of hot water preventing vacuum operation. In general, it is desirable to filter the slurry as hot as possible to reduce the risk of precipitation and deposit formation.

The exit temperature of the cooler was monitored by an online temperature transmitter, and controlled by manipulating the flow of town water with a control valve.

Filtering

After cooling, the slurry was discharged into the vat of a small vacuum drum filter through a control valve. This control valve was used to set the system pressure as monitored by the pressure transmitter. A three way automatic valve also allowed alternate discharge through a manual valve as a backup.

The slurry may also be discharged to drain by a three way automatic valve. This enables the whole system to be started on water or flushed out at the end of a run. This valve also allows the plant to keep operating for a short period should any problems arise with the filter.

The rotary drum filter included a vacuum pump and centrifugal pump. These collected and transferred the filtrate to and from a standpipe fitted with a level switch. The filtrate (hemicellulose liquor/sugar) from the standpipe was discharged into a collection tank for later use. The synthetic filter cloth had an air permeability of approximately 35 cfm and covered an area of 1858 $cm^2$.

The drum filter used a rocking agitator to prevent sedimentation of the slurry in the collection vat. The drum and agitator drive motors were controlled by locally operated variable speed drives, to enable the cake thickness and filter performance to be optimized.

The filter cake was removed from the synthetic cloth covered drum by an adjustable doctor blade, from which it fell under gravity into a water filled receival tank constantly stirred by an agitator to break up and suspend the filter cake. Prior to operation, that tank was filled with water via a flow indicator to a level above the stirrer preventing possible damage to the stirrer.

From the receival tank, the slurry (containing lignin and cellulose) was transferred over to a feed tank in a different reactor (for further processing) by an air operated diaphragm pump, the air to which is controlled by a solenoid valve.

Shower System

A shower bar installed above the drum was used to wash the product (hemicellulose liquor/sugar) solution from the filter cake to maximize recovery. The shower bar received hot town water from the cooler, reducing water consumption and enabling more effective washing over using cold water.

The flow of wash water was controlled by a control valve and an online flow meter. The control valve diverted the excess hot water not required by the shower bar to drain.

The flow of wash water was controlled to ratio of the feed rate, so that the flow was sufficient to displace the bound liquor in the filter cake only. In this manner, good washing was achieved without excess dilution of the product liquor.

The liberated hemicellulose may then undergo enzymatic de-polymerization and subsequent fermentation and distillation by established methods to produce ethanol. The remaining cellulose/lignin wood fractions can be collected as a solid and further treated.

Equipment Specifications
Plant Reactor Specifications:
The fundamental plant reactor operating specifications were as follows:
Feed Rate: 120 kg/hr of slurry per hour
Feed Consistency Maximum of 10% dry solids
Feed Size Maximum particle size 300 microns
Process Operating Pressure: 40 bar (gauge)
Process Design Pressure: 60 bar (gauge)
Process Design Temperature: 250° C.
Process Operating Pressure: 210° C.
Heat Exchanger Jacket Design Pressure: 20 bar
Heat Exchanger Jacket Design Temperature: 325° C.
Saturated Steam Delivery Pressure/Temperature: 10 bar (gauge); 180° C.

Example 3

Fractionation of Hemicellulose Liquor from Radiata Pine (*Pinus radiata*)

A series of different runs were performed in which hemicellulose liquor was extracted from Radiata pine (*Pinus radiata*). Different reaction conditions used for each of thirteen representative runs are described in Table 2 below.

Wood flour was prepared (150-300 microns) and combined with water in a batch tank to produce a slurry (5%-10% v/v solids concentration) which was then pumped into a reactor. The slurry was steam-heated to a temperature of 120° C.-210° C. and hemicellulose extracted at neutral PH, or under acidic conditions afforded by the addition of sulphuric acid (0.1%-0.4% wt) or carbon dioxide. Hemicellulose extraction reactions were performed for up to 10 minutes.

Upon completion of the reaction the mixture was passed through a filter to provide separate solid (lignin and cellulose) and liquid (hemicellulose and water) fractions. In some cases the solid fraction (filter cake) was washed to obtain residual hemicellulose liquor. The separated hemicellulose fraction was then analysed for sugar content as described in Examples 4 and 5 below.

TABLE 2

Reaction conditions for hemicellulose extraction from *P. radiata*

| Variable | Available range | Run Conditions | | | | | |
|---|---|---|---|---|---|---|---|
| | | 1 | 2 | 3 | 4 | 5 | 6 |
| Pressure (bar) | 22-60 | 40 | 40 | 40 | 30 | 30 | 30 |
| Temperature (° C.) | 120-210 | 120-210 | 120-210 | 120-210 | 120-190 | 120-190 | 120-190 |
| Solids Concentration (%) | 5-15% | 10 | 10 | 10 | 10 | 20 | 10 |
| Retention Time (min) | 0-10 | 10 | 5 | 0 | 10 | 20 | 10 |
| pH | 2-7 | 7 | 7 | 7 | ~2 | 7 | ~2 |
| Additives | Ethanol, phosphoric acid, sulphuric acid, carbon dioxide | None | None | None | 0.4% sulphuric acid | None | Carbon dioxide |
| Wood Flour Grade | 180 and 300 micron | 300 | 300 | 300 | 300 | 300 | 300 |
| Wood Species | *Radiata pine*, Oak | *Radiata pine* | *Radiata pine* | *Radiata pine* | *Radiata pine* | *Radiata pine* | *Radiata pine* |

| Variable | Available range | Run Conditions | | | | | |
|---|---|---|---|---|---|---|---|
| | | 7 | 8 | 9 | 10 | 11 | 12 |
| Pressure (bar) | 22-60 | 30 | 30 | 30 | 30 | 30 | 30 |
| Temperature (° C.) | 120-210 | 120-190 | 160-190 | 160-190 | 190 | 140-160 | 190 |
| Solids concentration (%) | 5-15% | 15% or greater | 10 | 10 | 10 | 10 | 10 |

TABLE 2-continued

Reaction conditions for hemicellulose extraction from *P. radiata*

| Retention Time (min) | 0-10 | 20 | 2.5 | 5 | 5 | 5 | 5 |
|---|---|---|---|---|---|---|---|
| pH | 2-7 | 7 | 7 | 7 | 7 | 7 | 7 |
| Additives | Ethanol, phosphoric acid, sulphuric acid, carbon dioxide | None | None | None | None | 0.1% wt sulphuric acid | None |
| Wood Flour Grade | 180 and 300 micron | 300 | 300 | 300 | 150 | 300 | 150 |
| Wood Species | Radiata pine, Oak | Radiata pine | Radiata pine | Radiata pine | Radiata pine | Radiata pine | Radiata pine |

Example 4

Production of Reducing Sugars from Hemicellulose Fraction Using Enzyme Hydrolysis Enzyme hydrolysis was conducted on hemicellulose liquor fractions obtained from Radiata pine samples by the process described in Example 3 above.

3.1 Materials and Methods

Conditions for enzyme hydrolysis were as shown in Table 3 below.

TABLE 3

Enzymatic hydrolysis of samples

| Sample Number | pH (liquor samples) | pH (with enzyme + buffer) | Temp. during sampling (°C.) | Extractives weight* (mg/mL) | Description/ Comments |
|---|---|---|---|---|---|
| 1.1 | 4.90 | 5.16 | RT | 5.2 | 10% FS |
| 1.2 | 3.82 | 4.8 | 190 | 12.0 | |
| 1.3 | 3.84 | 4.8 | 190 | 11.12 | |
| 1.4 | 4.12 | 4.96 | 150 | 11.68 | |
| 1.5 | 4.24 | 5.02 | 150 | 11.08 | |
| 1.6 | 4.37 | 5.11 | 130 | 7.76 | |
| 1.7 | 4.49 | 5.10 | 130 | 7.40 | |
| 2.1 | 4.75 | 5.15 | RT | 5.16 | 10% FS |
| 2.2 | 4.19 | 5.0 | 190 | 13.12 | |
| 2.3 | 4.21 | 5.0 | 190 | 13.08 | |
| 2.4 | 4.40 | 5.08 | 163 | 9.56 | |
| 2.5 | 4.46 | 5.12 | 163 | 8.44 | |
| 2.6 | 4.72 | 5.17 | 105 | 6.28 | |
| 2.7 | 4.62 | 5.20 | 105 | 5.68 | |

FS feedstock slurry;
RT room temperature
*based on dry weight from 25 mL of clear liquor samples dried in petri dish at 70° C., 14.5 hours Buffers and pH 120 mM of universal buffer (pH 6.5) was included in reaction mixes to provide optimal conditions for hydrolytic enzymes to act on hemicellulose present in the different fractions. The target pH during these assays was ~5-6. As shown in Table 3 above, the pH of each sample was measured before and after the addition of buffer and enzyme samples.

Hydrolytic Enzymes

A recombinant *Trichoderma reesei* strain was used to produce a mixture of hydrolytic enzymes comprising both hydrolytic fungal enzymes and a thermophilic xylanase (XynB).

Reaction Mixes

Reaction mixes for enzyme hydrolysis were prepared as follows:

| (i) Hemicellulose liquor samples | |
|---|---|
| Substrate | 500 μL |
| Enzyme | 300 μL |
| Univ. buffer (pH 6.5) | 200 μL |
| (ii) Substrate only control | |
| Substrate | 500 μL |
| Univ. buffer (pH 6.5) | 200 μL |
| H$_2$O | 300 μL |
| (iii) Enzyme only control: | |
| Enzyme | 300 μL |
| Univ. buffer (pH 6.5) | 200 μL |
| H$_2$O | 500 μL |

All tubes were incubated at 50° C. (with rotation) for 1.5 hours then removed and kept at 4° C.

Colorimetric Reducing Sugar Assay

A colourimetric dinitrosalicyclic acid (DNS)-reducing sugar assay was used as an indicator of enzyme hydrolysis (see Bailey and Poutanen (1989), "*Production of xylanases by strains of Aspergillus*", Appl. Microbiol. Biotechnol. 30: 5-10), The DNS reducing sugar method tests for the presence of free carbonyl groups (C=O), present on reducing sugars (e.g. glucose, xylose, mannose, etc). As a result, 3,5-dinitrosalicyclic acid (DNS) is reduced to 3-amino,5-nitrosalicyclic acid under alkaline conditions and an intense orange-brown colour is formed, indicative of reducing sugars, etc.

50 μL of sample was collected from each tube after enzyme hydrolysis, mixed with 75 μL DNS and boiled for 5 minutes. Absorbance I$_{540}$ was read from 100 μL samples.

3.2 Results

Colorimetric Reducing Sugar Assay

Absorbance readings obtained from the 100 μL samples labelled 1.1-1.7 and 2.1-2.7 were plotted and are shown in FIG. 1. These results are indicative of the presence and subsequent increase in reducing ends following hydrolysis with the mixture of hydrolytic enzymes utilised.

Example 5

Total Sugar-Acid Hydrolysis and Analysis by High Performance Liquid Chromatography (HPLC)

Enzyme hydrolysis was conducted on hemicellulose liquor fractions obtained from Radiata pine samples by the process described in Example 3 above.

4.1 Materials and Methods

Total sugar analysis of was performed according to the Standard Test Method for Carbohydrate Distribution of Cellulosic Materials, TAPPI Standard, Designation: D 5896-96 (2007), with some minor modifications.

In brief, samples were prepared as follows:
1. Liquor samples (containing 100 mg total extractives, see Table 3) were transferred into a 20×150 mm glass culture tubes and dried using an oven set at 75° C.
2. 1 mL of cold 72% sulfuric acid was added to each tube containing 100 mg of extractives/carbohydrate (bone dry basis), carefully mixed, then incubated in refrigerator overnight (4° C.).
3. Samples were heated at 30° C. for 1 hour followed by addition of 28 mL of MilliQ-$H_2O$
4. Samples were autoclaved at 121° C. for 1 hour (wet run) then cooled to room temperature.
5. 20-25 mL supernatant was removed and centrifuged at 13,500 rpm for 30-60 minutes at room temperature.
6. Clear supernatant was removed for analysis, or stored at −20° C.

High performance liquid chromatography was then performed at the Australian Proteome Analysis Facility (APF, see Worldwide Website: proteome.org.au).

4.2 Results

Total Sugar-Acid Hydrolysis and HPLC Analysis

Tables 4-9 summarise total sugar concentration calculations and molecular ratios of the different types of mono sugars in hemicellulose liquor samples subjected to acid hydrolysis. Results are summarised in Table 10.

TABLE 4

Detected amount by HPAEC-PAD (pmol)

|  | Sample (i) | Sample (i) (control) | Sample (ii) | Sample (ii) (control) |
|---|---|---|---|---|
| Ara | 192 | 220 | 112 | 223 |
| Gal | 329 | 35 | 332 | 52 |
| Glc | 319 | 91 | 298 | 36 |
| Xly | 132 | 49 | 346 | 90 |
| Man | 465 | 21 | 756 | 29 |
| Fru | 0 | 87 | 0 | 0 |

TABLE 5

Concentration of sample diluted with water to 1/50 (uM)

|  | Sample (i) | Sample (i) (control) | Sample (ii) | Sample (ii) (control) |
|---|---|---|---|---|
| Ara | 19 | 22 | 11 | 22 |
| Gal | 33 | 4 | 33 | 5 |
| Glc | 32 | 9 | 30 | 4 |
| Xly | 13 | 5 | 35 | 9 |
| Man | 46 | 2 | 76 | 3 |
| Fru | 0 | 9 | 0 | 0 |

TABLE 6

Concentration of sample (uM, x 50 dilution factor)

| MW |  | Sample (i) | Sample (i) (control) | Sample (ii) | Sample (ii) (control) |
|---|---|---|---|---|---|
| 150.13 | Ara | 959 | 1100 | 561 | 1117 |
| 180.16 | Gal | 1647 | 176 | 1658 | 261 |
| 180.2 | Glc | 1593 | 456 | 1489 | 182 |
| 150.1 | Xly | 661 | 247 | 1731 | 448 |
| 180.16 | Man | 2325 | 105 | 3780 | 147 |
|  | SUM | 7184 | 2083 | 9218 | 2154 |

TABLE 7

Molecular ratio (%)

|  | Sample (i) | Sample (i) (control) | Sample (ii) | Sample (ii) (control) |
|---|---|---|---|---|
| Ara | 13 | 53 | 6 | 52 |
| Gal | 23 | 8 | 18 | 12 |
| Glc | 22 | 22 | 16 | 8 |
| Xly | 9 | 12 | 19 | 21 |
| Man | 32 | 5 | 41 | 7 |
| SUM | 100 | 100 | 100 | 100 |

TABLE 8

Weight in 29 mL (mg)

|  | Sample (i) | Sample (i) (control) | Sample (ii) | Sample (ii) (control) |
|---|---|---|---|---|
| Ara | 4.2 | 4.8 | 2.4 | 4.9 |
| Gal | 8.6 | 0.9 | 8.7 | 1.4 |
| Glc | 8.3 | 2.4 | 7.8 | 0.9 |
| Xly | 2.9 | 1.1 | 7.5 | 1.9 |
| Man | 12.1 | 0.5 | 19.7 | 0.8 |
| SUM | 36.1 | 9.7 | 46.2 | 9.9 |

TABLE 9

Weight ratio (%)

|  | Sample (i) | Sample (i) (control) | Sample (ii) | Sample (ii) (control) |
|---|---|---|---|---|
| Ara | 12 | 49 | 5 | 49 |
| Gal | 24 | 9 | 19 | 14 |
| Glc | 23 | 25 | 17 | 10 |
| Xly | 8 | 11 | 16 | 20 |
| Man | 34 | 6 | 43 | 8 |
| SUM | 100 | 100 | 100 | 100 |

TABLE 10

Overview of total sugar-acid hydrolysis

| | Concentration (μM) | | | | Weight ratio (%) | | | |
|---|---|---|---|---|---|---|---|---|
| Sugar | Sample (i) | Sample (i) control | Sample (ii) | Sample (ii) control | Sample (i) | Sample (i) control | Sample (ii) | Sample (ii) control |
| Ara | 959 | 1100 | 561 | 1117 | 12 | 49 | 5 | 49 |
| Gal | 1647 | 176 | 1658 | 261 | 24 | 9 | 19 | 14 |

TABLE 10-continued

Overview of total sugar-acid hydrolysis

| Sugar | Concentration (μM) | | | | Weight ratio (%) | | | |
|---|---|---|---|---|---|---|---|---|
| | Sample (i) | Sample (i) control | Sample (ii) | Sample (ii) control | Sample (i) | Sample (i) control | Sample (ii) | Sample (ii) control |
| Glc | 1593 | 456 | 1489 | 182 | 23 | 25 | 17 | 10 |
| Xyl | 661 | 247 | 2325 | 105 | 8 | 11 | 16 | 20 |
| Man | 2325 | 105 | 3780 | 147 | 34 | 6 | 43 | 8 |
| SUM | 7184 | 2083 | 9218 | 2154 | 100 | 100 | 100 | 100 |

HPLC results demonstrated that each sample analysed was a hemicellulose fraction based on the type and ratio of mono sugars released following acid hydrolysis. Assuming a 100 mg of total mono sugars, the percentage ratios of the main sugars following acid hydrolysis for sample (ii) were as follows: Man:Gal:Glc:Xyl:Ara=43:19:17:16:5.

Example 6

Extraction of Hemicellulose from Wood Flour Slurry and Stabilisation of Lignin/Cellulose Composite to Produce a Bio-Oil Product A stepwise process was used to extract hemicellulose from woodflour feed and produce a stable oil from the remaining lignin/cellulose composite.

Woodflour Slurry Preparation

Woodflour slurry for hemicellulose extraction was prepared from approximately 25 kg of woodflour. Water was added such that the resulting slurry contained approximately 18% woodflour and 82% water.

Hemicellulose Extraction

Hemicellulose was extracted from the slurry as described in Example 2 above using the following conditions:
reactor temperature 190° C.,
reactor pressure 31 bar,
residence time 5 minutes,
woodflour size 150 microns (in water).

The resultant filter cake (containing lignin and cellulose) was transferred to another reactor for further processing.

Conversion of Lignin/Cellulose to Bio-Oil Product

Filter cake containing lignin and cellulose composite derived from pre-processing was subjected to treatment with aqueous ethanol in a reactor. Reaction conditions were as follows:

| | |
|---|---|
| Reactor Temperature: | 320° C. |
| Reactor Pressure: | 200 bar |
| Woodflour Slurry Ratio Estimate (by weight): | 5% |
| Additives-Ethanol (80 L) | 25% by volume |
| Residence time | 18 minutes |

Analysis of Bio-Oil Emulsion

The sample analyzed was water-based and contained in a PET bottle. It took the form of an orange-coloured emulsion. Some brown oil/tar was coated on the wall of the bottle. A small amount of the orange emulsion was shaken with diethyl ether, resulting in a brown ether layer and a clear, slightly coloured lower (aqueous) layer. The ether layer was analysed by gas chromatography mass spectrometry (GCMS) as was the brown oil/tar phase, also dissolved in ether.

Gas Chromatography Mass Spectrometry (GCMS) Results

GCMS chromatograms revealed the presence of many compounds in the emulsion. Larger peaks in the GCMS reports were integrated automatically and the mass spectra associated with the peaks compared with a spectral library. The library compound with the closest spectral match was then assigned to the peak by the software. Examples of compounds that were matched with a high degree of confidence include:

(i) Compounds in emulsion:

phenol, 2-cyclopentene-1-one, 2-methyl, methoxyphenol, ethylmethoxyphenol, methoxypropylphenol.

(ii) Compounds in oil:

methoxyphenol, ethylmethoxyphenol, methoxypropenylphenol

Proton NMR Analysis

The oil sample was dissolved in d6-acetone and the proton NMR spectrum recorded. Some of the remaining emulsion/water phase was extracted with diethyl ether which was then removed under reduced pressure to give an orange-brown oil "ether extract". The sample was dissolved in d6-acetone and the proton NMR spectrum recorded.

The NMR spectra of the brown oil/tar and the ether extract were complex. The spectrum of the oil in particular had broad, ill-defined peaks. The spectrum of the ether extract was divided approximately into 5 chemical shift regions so that the signals could be integrated providing an approximate idea of the types and relative abundances of functional groups present could be obtained (see Table 11). These abundances were rounded to the nearest whole number (except for the first row) and the possible presence of residual solvent signals (ether, ethanol, isopropanol, acetone, water) disregarded, as were inaccuracies in the integration.

TABLE 11

NMR spectra analysis

| Possible chemical environment of proton | Approximate relative abundance of protons | Chemical shift range |
|---|---|---|
| ArOH or RCHO | 0.5 | 9+ |
| Aromatic or olefin | 7 | 9-5 |
| Adjacent to oxygen | 4 | 5-3 |
| Methylene or aromatic methyl | 6 | 3-1.2 |
| Methyl | 3 | <1.2 |

A complex mixture of this nature cannot be represented by a small number of compounds. For conceptual purposes, an equimolar mixture of the two compounds below may produce similar integrations for the chemical shift regions in the Table 11 above (NB: ArOH/RCHO protons were disregarded for this purpose).

The estimated chemical shifts of the protons are shown below:

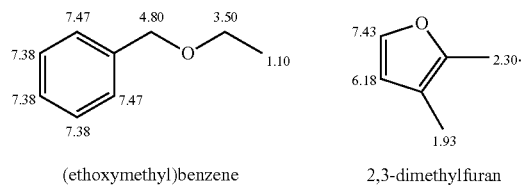

(ethoxymethyl)benzene    2,3-dimethylfuran

It was also observed that no wood slurry appeared to be present in the product emulsion inferring that all the slurry has been converted to oil and potentially gaseous products.

Example 7

Production of Bio-Oil from Radiata Pine Wood Flour (i) Reaction Conditions

To improve the quality of the bio-oil product, the effect of varying reactor retention time and various reaction conditions was tested on radiata pine wood flour stripped of hemicellulose (see Example 2 above) in a mixture of water and 5-20% wt ethanol under pressure.

Trials were conducted under the various conditions shown in Table 12. Table 12 lists the target temperature and pressure at which the pilot plant conditions were maintained as close to as practicable.

TABLE 12 variations in reaction conditions

| Reactor Retention (minutes) | Target Pressure (bar) | Target Temperature (° C.) | Slurry Solids Concentration (% wt) |
|---|---|---|---|
| 15 | 120-240 | 280-350 | 4-30 |
| 5 | 120-240 | 280-350 | 4-30 |
| 30 | 120-240 | 280-350 | 4-30 |

In each case, the wood flour was successfully processed to generate a liquid product containing two phases:
1. A lighter aqueous phase containing lighter dissolved organics which could be extraction to produce a mobile light oil.
2. A heavier black oil phase.

(ii) Analyses of Product

Black Oil Phase

Figure 2:
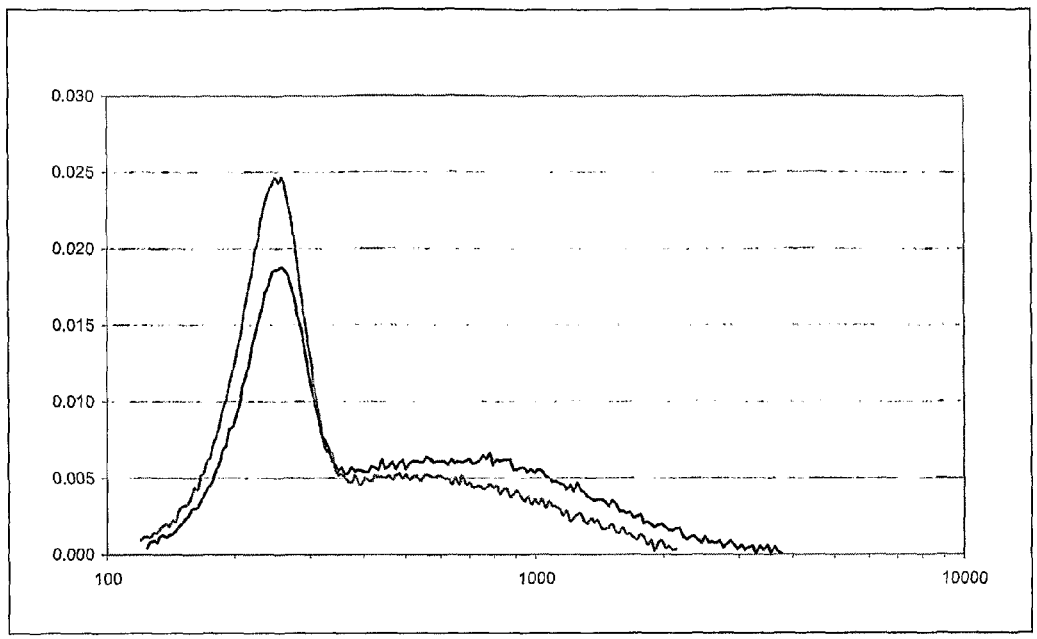
FIG. 2 is a graph showing the results of a gel permeation chromatography (GPC) analysis of a heavy oil fraction produced in accordance with the methods of the invention. Vertical axis: normalised intensity; horizontal axis: molecular weight; light trace: 15 minute retention time; dark trace: 30 minute retention time.

Samples of the heavier oil produced from 15 and 30 minutes reactor retentions were analysed using gel permeation chromatography (GPC) to provide an indication of molecular weight distributions of various compounds within the heavy oil. The typical measured distributions are shown in FIG. 2.

The GPC results show that increasing retention time decreases the molecular weight distribution, resulting in lighter oil.

A sample of the heavier oil produced from 15 minutes reactor retention was dried removing the bound water by distillation and an ultimate analysis then performed on the dry sample. The elements tested and measured weight fractions are reported in Table 13. On a dry basis, radiata pine is typically 40% oxygen by weight. From the results it can be seen that the heavy oil sample can be no more than 19% oxygen as determined by difference. This represents at least 50% reduction in oxygen content compared to the feedstock, greatly increasing the energy of the heavy oil compared to the starting feedstock.

TABLE 13

Ultimate Analysis of 30 minute retention heavier oil

| Element | Weight Fraction |
|---|---|
| Carbon | 74.71% |
| Hydrogen | 6.39% |
| Nitrogen | 0.00% |
| Sulphur | 0.00% |

Figure 3:
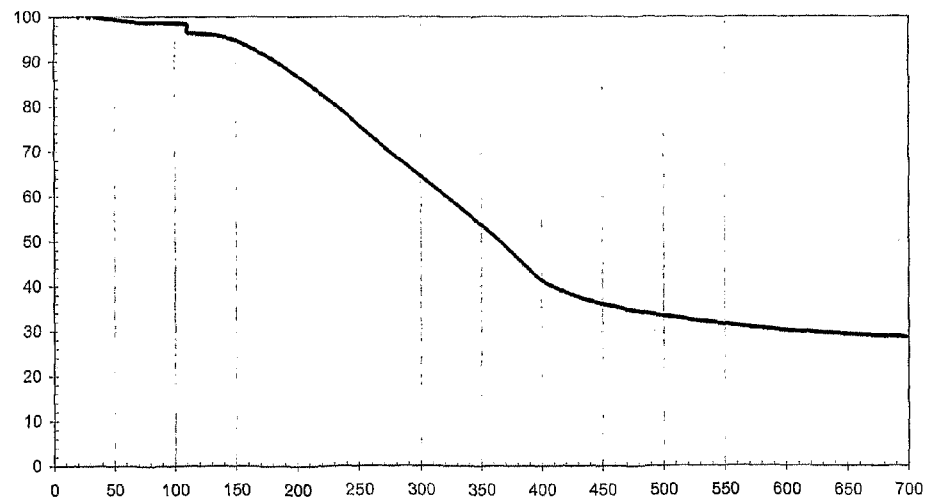
FIG. 3 is a graph showing the results of thermo gravimetric analysis (TGA) of a heavy oil fraction produced in accordance with the methods of the invention. Vertical axis: percentage of mass lost; horizontal axis: temperature (° C.); trace: represents results from heavy oil produced using a 30 minute retention time.

A sample of the heavy oil produced from 30 minutes reactor retention was used for Thermo gravimetric analysis (TGA). Thermo gravimetric analysis (TGA) measures the mass lost from a sample during heating in a flow of dry nitrogen. As indicated by the results in FIG. 3, the heavier oil has a very broad boiling point range, and is quite volatile until approximately 400° C.

GCMS is a technique that can be used to identify compounds. A gas chromatograph (GC) is used to separate the individual compounds in a sample and the output from the GC is then fed into a mass spectrometer (MS) which ionizes the compounds and measures the mass to charge ratio of the fragments. The data is then matched against a library to provide a probable identification of the compounds.

Figure 4:
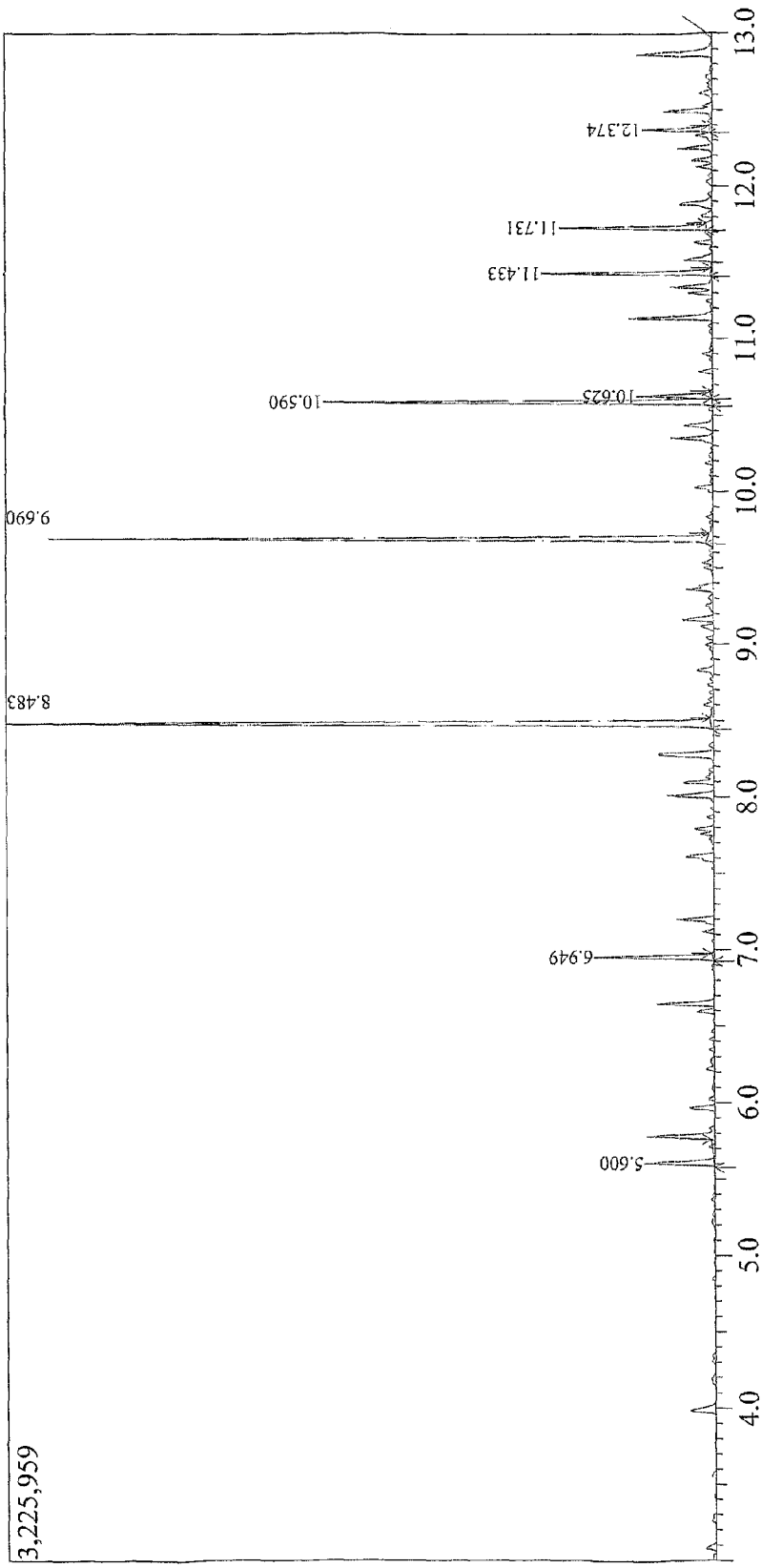
FIG. 4 is a chromatogram showing the results of a gas chromatography-mass spectroscopy (GCMS) analysis of diethyl ether-extractable oils derived from the aqueous phase of an oil emulsion produced in accordance with the methods of the invention. Peaks: 2.342 (Ether,1-propenyl propyl), 5.600 (2-Cyclopenten-1-one, 2-methyl-), 6.949 (Phenol), 8.483 (Phenol, 2-methoxy-), 9.690 (2,3-Dimethylhydroquinone), 10.590 (Phenol, 4-ethyl-2-methoxy-), 10,625 (1,2-Benzenediol, 4-methyl-), 11.433 (Phenol, 2-methoxy-4-propyl-), 11.731 (Vanillin), 12.374 (Phenol, 2-methoxy-).
Figure 5:
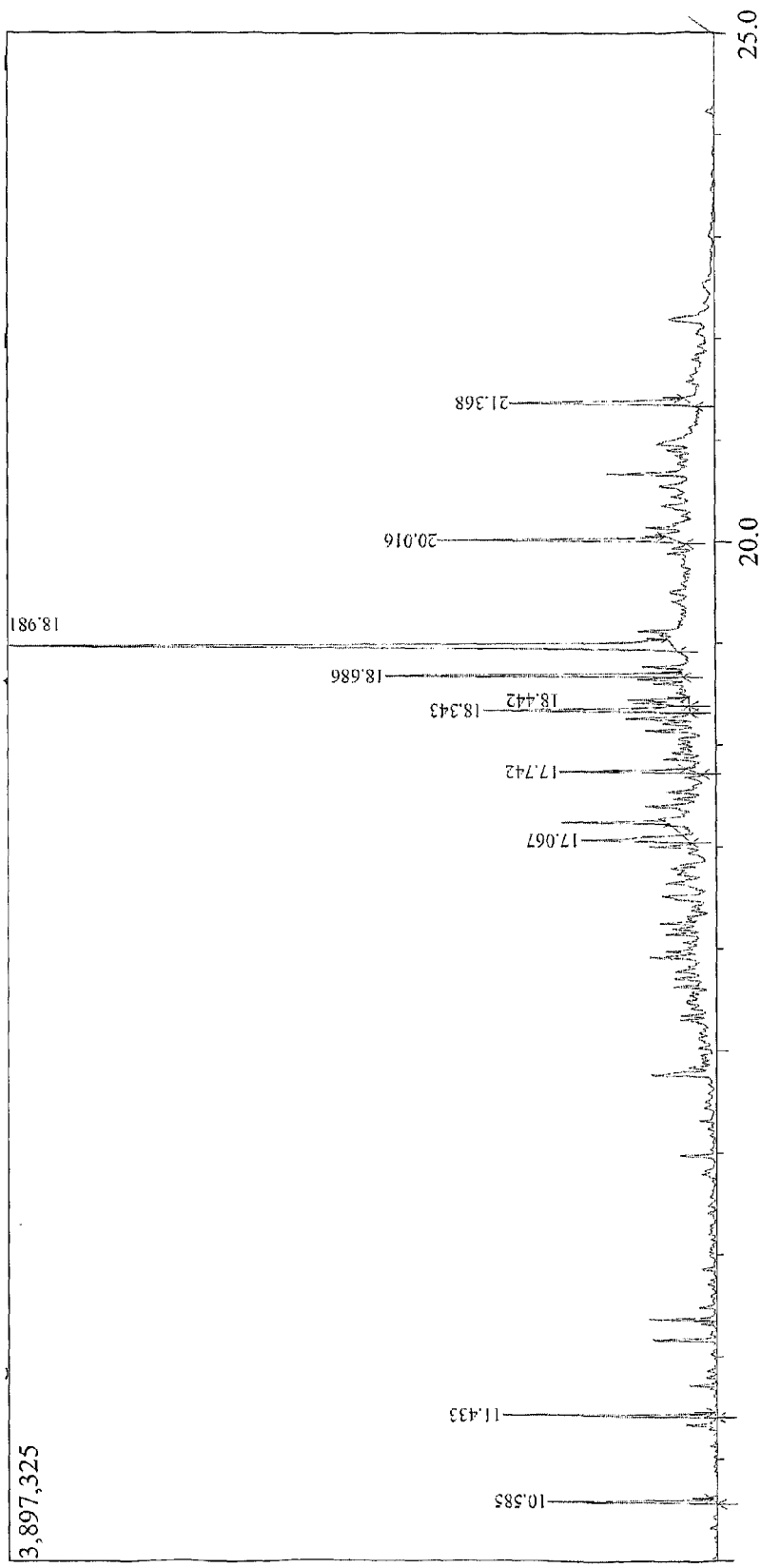
FIG. 5 is a chromatogram showing the results of a gas chromatography-mass spectroscopy (GCMS) analysis of a heavy oil fraction produced in accordance with the methods of the invention dissolved in tetrahydrofuran. Peaks: 10.585 (Phenol, 4-ethyl-2-methoxy-), 11.433 (Phenol, 2-methoxy-4-propyl-), 17.067 (Oleic Acid), 17.742 (2-Isopropyl-10-methylphenanthrene), 18.343 (3-(3-Hydroxy-4-methoxyphenyl)-1-alanine), 18.442 ((−)-Nortrachelogenin), 18.686 (1-Phenanthrenecarboxylic acid, 1,2,3,4,4a,9,10,10a-octahydro-1,4-a-dimethyl-7-(1-methylethyl)-, methyl ester, [1R-(1.alpha., 4a.beta., 10a.alpha.)]), 18.981 (1-Phenanthrenecarboxylic acid, 1,2,3,4,4a,9,10,10a-octahydro-1,4-a-dimethyl-7-(1-methylethyl)-, [1R-(1.alpha., 4a.beta., 10a.alpha.)]), 20.016 (7-(3,4-Methylenedioxy)-tetrahydrobenzofuranone), 21.368 (Carinol).

FIGS. 4 and 5 show data provided by GCMS analysis of the aqueous and heavier oil phases from the 30 minute retention products. Hundreds of compounds are present, and the largest 10 peaks based on area have been assigned from the NIST spectral library. The assignments provide an indication as to the nature of the oils which are largely oxygenated aromatics. FIG. 4 shows the results of GCMS analysis of the aqueous phase. FIG. 5 shows the results of GCMS analysis of the heavier oil phase.

The invention claimed is:

1. A method for producing a bio-oil from lignocellulosic matter, the method comprising the steps of:
    (a) solvating hemicellulose from the lignocellulosic matter using a solvent;
    (b) removing solvated hemicellulose from solid matter comprising lignin and cellulose remaining after step (a); and
    (c) solvating both of the lignin and the cellulose of the solid matter together using a solvent at a reaction temperature of between 260° C. and 350° C. and a reaction pressure of between 8 MPa and 26 MPa,
wherein step (c) of solvating both of the lignin and the cellulose together at said reaction temperature and said reaction pressure converts the lignin and the cellulose into a product comprising an aqueous phase and an oil phase comprising the bio-oil; and
    wherein the bio-oil is produced in the absence of fermentation or enzymatic hydrolysis of said lignocellulosic matter.

2. The method according to claim 1, wherein said lignocellulosic matter comprises 10%-35% hemicellulose, 15%-45% cellulose and 2%-35% lignin.

3. The method according to claim 1, wherein said lignocellulosic matter comprises 20%-35% hemicellulose, 20%-45% cellulose and 20%-35% lignin.

4. The method according to claim 1, wherein the solvent of step (c) is an aqueous alcohol comprising no more than ten carbon atoms.

5. The method according to claim 4, wherein the aqueous alcohol is ethanol or methanol.

6. The method according to claim 4, wherein the aqueous alcohol comprises 1%-30% alcohol by weight.

7. The method according to claim 4, wherein the aqueous alcohol comprises about 20% alcohol by weight.

8. The method according to claim 1, wherein step (c) is performed at a reaction temperature of between 280° C. and 350° C.

9. The method according to claim 1, wherein step (c) is performed at a temperature of about 320° C.

10. The method according to claim 1, wherein step (c) is performed at a reaction pressure of between 12 MPa and 24 MPa.

11. The method according to claim 1, wherein step (c) is performed at a reaction pressure of about 20 MPa.

12. The method according to claim 1, wherein the lignin and cellulose of step (c) is in the form of a slurry comprising between 2% and 45% solid matter by weight.

13. The method according to claim 12, wherein the slurry comprises about 10% solid matter by weight.

14. The method according to claim 1, wherein step (c) is performed for between 2 minutes and 60 minutes.

15. The method according to claim 1, wherein step (c) is performed for between 5 minutes and 30 minutes.

16. The method according to claim 1, wherein the solvating of hemicellulose in step (a) is performed at a reaction temperature of between 100° C. and 250° C., and a reaction pressure of between 0.2 MPa and 5 MPa.

17. The method according to claim 1, wherein the solvent of step (a) is:
(i) an aqueous acid and the treatment is performed at a pH of below about 6.5;
(ii) an aqueous base and the treatment is performed at a pH of above about 7.5; or
(iii) water.

18. The method according to claim 1, further comprising pre-treating the lignocellulosic matter prior to solvating hemicellulose in step (a), wherein the pre-treating comprises producing a slurry comprising a mixture of a solvent and particles derived from the lignocellulosic matter.

19. The method according to claim 18, wherein said particles are between about 100 microns and about 1000 microns in size.

20. The method according to claim 18, wherein the slurry comprises between about 5% and about 20% lignocellulosic matter.

21. A method for producing a bio-oil from lignocellulosic matter, the method comprising the steps of:
(a) solvating hemicellulose from the lignocellulosic matter using a solvent;
(b) removing solvated hemicellulose from solid matter remaining after step (a); and
(c) solvating a slurry comprising between 2% and 45% solid matter by weight and comprising lignin and cellulose obtained from the material obtained in step (b) using a solvent at a reaction temperature of between 260° C. and 350° C. and a reaction pressure of between 8 MPa and 26 MPa to produce a bio-oil;
wherein the lignin and cellulose are solvated together at said reaction pressure and temperature thereby converting the lignin and the cellulose into the bio-oil, and the method does not comprise enzymatic hydrolysis of cellulose to produce sugar units and fermentation of the sugar units by a microorganism to provide a bio-alcohol.

* * * * *

UNITED STATES PATENT AND TRADEMARK OFFICE
CERTIFICATE OF CORRECTION

| | | Page 1 of 1 |
|---|---|---|
| PATENT NO. | : 9,005,312 B2 | |
| APPLICATION NO. | : 13/121960 | |
| DATED | : April 14, 2015 | |
| INVENTOR(S) | : Len Humphreys | |

It is certified that error appears in the above-identified patent and that said Letters Patent is hereby corrected as shown below:

In the specification

Column 4,
Line 40, "a shiny" should read --a slurry--.

Column 9,
Line 6, "grass dippings," should read --grass clippings,--.

Column 30,
Lines 34-35, "*Saccharomyces Candida* sp." should read
    --*Saccharomyces* sp., *Candida* sp.--.

Column 33,
Line 34, in the equipment specifications, "Feed Consistency Maximum" should read --Feed Consistency: Maximum--.

Column 34,
Line 1, in the equipment specifications, "Feed Size Maximum" should read --Feed Size: Maximum--.

Signed and Sealed this
Twenty-second Day of March, 2016

Michelle K. Lee
*Director of the United States Patent and Trademark Office*